US008461543B2

(12) United States Patent
Nishino

(10) Patent No.: US 8,461,543 B2
(45) Date of Patent: Jun. 11, 2013

(54) RADIOGRAPHIC IMAGE CAPTURING SYSTEM

(75) Inventor: Naoyuki Nishino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 108 days.

(21) Appl. No.: 12/869,785

(22) Filed: Aug. 27, 2010

(65) Prior Publication Data

US 2011/0057111 A1 Mar. 10, 2011

(30) Foreign Application Priority Data

Sep. 3, 2009 (JP) ................................. 2009-203705
Jul. 28, 2010 (JP) ................................. 2010-169734

(51) Int. Cl.
*G01T 1/24* (2006.01)

(52) U.S. Cl.
USPC .................................................. 250/370.08

(58) Field of Classification Search
USPC .................................................. 250/370.08
See application file for complete search history.

(56) References Cited

U.S. PATENT DOCUMENTS

| 5,844,242 | A * | 12/1998 | Jalink et al. ............... 250/370.09 |
| 6,175,611 | B1 * | 1/2001 | Melen et al. ..................... 378/19 |
| 6,273,606 | B1 * | 8/2001 | Dewaele et al. ............... 378/174 |
| 7,555,100 | B2 * | 6/2009 | Wang et al. ................ 378/98.12 |
| 2003/0072414 | A1 * | 4/2003 | Sakaida ....................... 378/98.8 |
| 2004/0234032 | A1 * | 11/2004 | Nokita ......................... 378/98.8 |
| 2008/0226031 | A1 * | 9/2008 | Yokoyama et al. .......... 378/98.7 |
| 2009/0080756 | A1 * | 3/2009 | Chang et al. .................. 382/132 |

FOREIGN PATENT DOCUMENTS

| JP | 2002-85392 A | 3/2002 |
| JP | 2005-257634 A | 9/2005 |
| JP | 2006-500126 T | 1/2006 |
| JP | 2008-17965 A | 1/2008 |

* cited by examiner

*Primary Examiner* — Marcus Taningco
(74) *Attorney, Agent, or Firm* — SOLARIS Intellectual Property Group, PLLC

(57) ABSTRACT

A radiographic image capturing system includes plural radiographic image capturing devices that carry out an image capturing preparation operation when capturing a radiographic image; and a synchronous control section that carries out control that synchronizes the image capturing preparation operations of the plurality of radiographic image capturing devices.

10 Claims, 30 Drawing Sheets

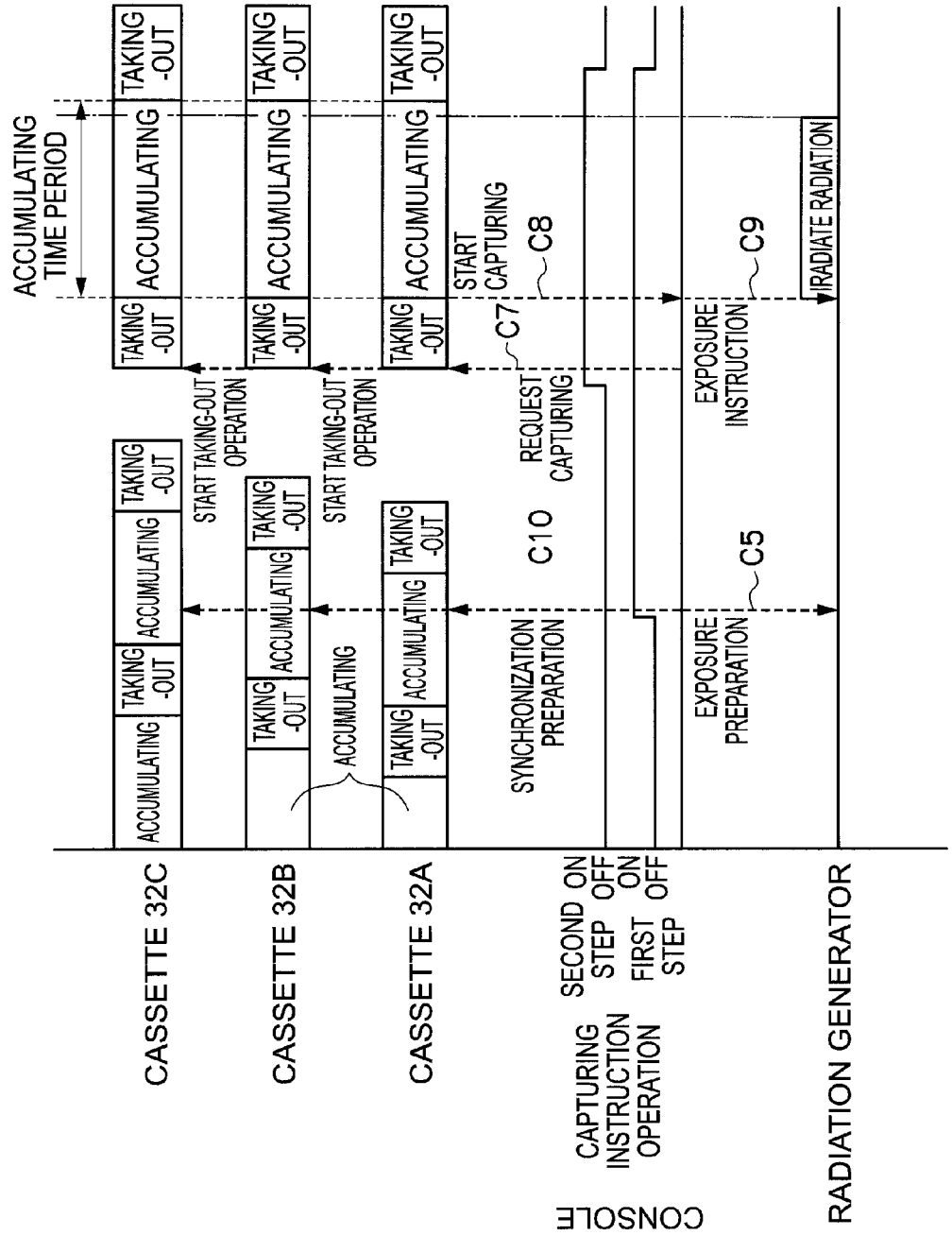

RADIOGRAPHIC IMAGE CAPTURING SYSTEM

CROSS-REFERENCE TO RELATED APPLICATION

This application claims priority under 35 USC 119 from Japanese Patent Applications Nos. 2009-203705 and 2010-169734 respectively filed on Sep. 3, 2009, and on Jul. 28, 2010, the disclosures of which are incorporated by reference herein.

BACKGROUND OF THE INVENTION

1. Field of the Invention

The present invention relates to a radiographic image capturing system.

2. Description of the Related Art

Radiation detectors such as Flat Panel Detectors (FPDs), in which a radiation-sensitive layer is disposed on a Thin Film Transistor (TFT) active matrix substrate and that can convert radiation directly into digital data, have been put into practice in recent years. Accompanying this, the digitization of radiographic image capturing systems has advanced, and industries are transitioning from films and imaging plates to radiation detectors.

As compared with films and imaging plates, a radiation detector is expensive but results in high image quality, and further, has the advantage that images can be confirmed immediately. The popularization of radiation detectors is thereby advancing.

In radiographic image capturing, in addition to a method of capturing a region to be captured in a single image, there is also a method of capturing an elongated image by dividing the region to be captured (e.g., the entire body), that cannot fit into a single image, into plural images. In a radiographic image capturing system using a film or an imaging plate, a method is proposed of preparing plural cassettes that house films or imaging plates, and carrying out image capturing by partially overlapping the plural cassettes so as to make the surface area of image capturing larger (see, for example, Japanese Patent Applications Laid-Open (JP-A) Nos. 2002-85392 and 2005-257634). In a radiographic image capturing system using a radiation detector, not only is the radiation detector expensive, but also, the radiation detector is thick as compared with other systems. Therefore, there is proposed a method of carrying out exposure plural times while moving a single radiation detector and changing the range of image capturing so as to capture plural images, and thereafter, combining the plural images into a single image (see, for example, JP-A No. 2008-17965 and Japanese Patent Application National Publication No. 2006-500126).

However, the image capturing methods of JP-A No. 2008-17965 and Japanese Patent Application National Publication No. 2006-500126 require that exposure of X-rays be carried out plural times, and the image capturing time from the start of image capturing to the end thereof is long. Therefore, due to movement of the patient's body, combining of the images may fail, and patients with ailments must maintain the same body position over a long period of time. Therefore, a large burden is placed on the patient.

In recent years, there have been proposed thin cassettes (hereinafter also called "electronic cassettes") that use a radiation detector. In the same way as with cassettes using films or imaging plates, an elongated image can be captured by connecting plural electronic cassettes, and the problem of the image capturing time becoming long can be overcome.

However, at a radiation detector, even in a state in which X-rays are not being irradiated, charges are generated due to dark current or the like, and the charges are accumulated in sensor portions that detect the X-rays. Therefore, during standby for imaging capturing, a radiation detector repeatedly and periodically carries out various image capturing preparation operations such as an eliminating operation that takes-out and eliminates the charges accumulated in the sensor portions.

It is not simple for plural radiographic image capturing devices, that repeatedly and periodically carry out such image capturing preparation operations, to simultaneously carry out capturing of radiographic images, which is different than in cases of using films or imaging plates.

SUMMARY OF THE INVENTION

In view of the aforementioned, the present invention provides a radiographic image capturing system that can simultaneously carry out capturing of radiographic images at plural radiographic image capturing devices that carry out a predetermined image capturing preparation operation before capturing a radiographic image.

A first aspect of the present invention is a radiographic image capturing system having: plural radiographic image capturing devices that carry out an image capturing preparation operations when capturing a radiographic image; and a synchronous control section that carries out control that synchronizes the image capturing preparation operations of the plural radiographic image capturing devices.

In accordance with the present aspect, by synchronizing the image capturing preparation operations of the plural radiographic image capturing devices, image capturing of radiographic images at the plural radiographic image capturing devices can be carried out simultaneously.

In the above-described structure, the synchronous control section may synchronize the image capturing preparation operations of the plurality of radiographic image capturing devices by notifying the plural radiographic image capturing devices of a cycle to be synchronized with, or once suspend the image capturing preparation operations and re-starting the image capturing preparation operations in synchronization.

In the above-described structure, the radiographic image capturing device may have: a radiation detector having plural sensor portions that accumulate charges generated due to irradiation being irradiated from a radiation source; and a detector control section that controls the radiation detector to repeatedly carry out, as the image capturing preparation operation, an accumulating/taking-out operation that takes-out charges accumulated in the respective sensor portions of the radiation detector in a state in which radiation is not irradiated from the radiation source, and the synchronous control section may synchronize cycles of the accumulating/taking-out operations of the plural radiographic image capturing devices.

In the above-described structure, the synchronous control section may synchronize the cycles of the accumulating/taking-out operations of other radiographic image capturing devices with the cycle of the accumulating/taking-out operation of any one of the radiographic image capturing devices.

In the above-described structure, the synchronous control section may be provided at each of the radiographic image capturing devices; and the radiographic image capturing device may further have a communication unit that makes possible communication with the synchronous control sections provided at the respective radiographic image capturing devices.

In the above-described structure, the radiographic image capturing system may further have: a detecting section that detects degrees of overlap of radiographic image capturing regions of the plural radiographic image capturing devices; and a limiting section that limits a region onto which radiation is irradiated from the radiation source, in accordance with the degrees of overlap of the radiographic image capturing regions detected by the detecting section.

In the above-described structure, the radiographic image capturing system may further have: a judging section that judges whether or not the image capturing preparation operations of the plural radiographic image capturing devices are synchronous; and a permitting section that permits irradiation of radiation onto the plural radiographic image capturing devices, in a case in which the judging section judges that the image capturing preparation operations are synchronous.

In the above-described structure, the radiographic image capturing system may further have: a judging section that judges whether or not the image capturing preparation operations of the plural radiographic image capturing devices are synchronous; and a notification section that gives notice of results of judgment by the judging section.

In accordance with the present invention, capturing of radiographic images can be carried out simultaneously at plural radiographic image capturing devices that repeatedly and periodically carry out an image capturing preparation operation.

BRIEF DESCRIPTION OF THE DRAWINGS

Exemplary embodiments of the present invention will be described in detail based on the following figures, wherein:

FIG. 30 is a timing chart showing a change in operation timings of three electronic cassettes according to a synchronous control processing of the fifth exemplary embodiment.

DETAILED DESCRIPTION OF THE INVENTION

Exemplary embodiments are described in detail hereinafter with reference to the drawings. Note that, here, explanation is given of embodiments as a radiology information system that is a system that collectively manages information that is handled in the radiology department of a hospital.

First Exemplary Embodiment

Figure 1:
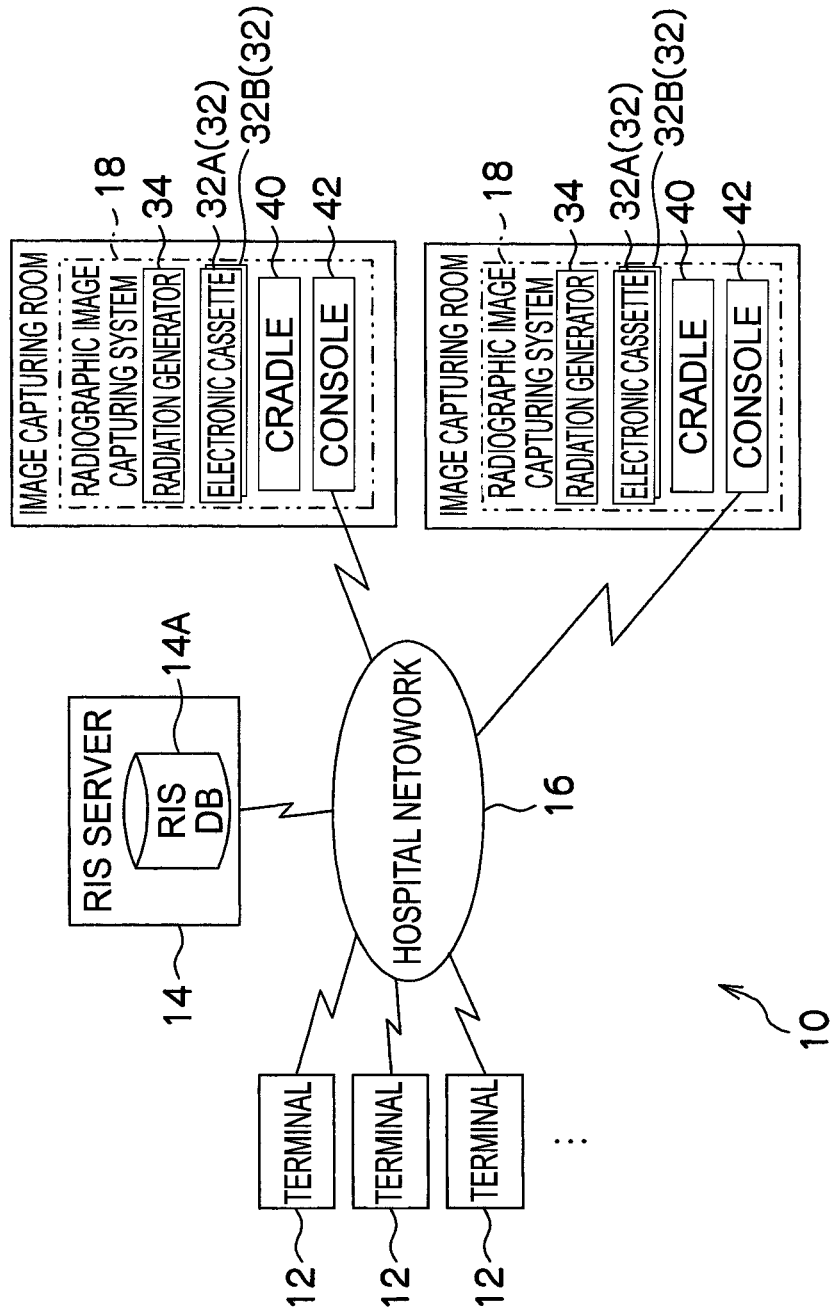
FIG. 1 is a block diagram showing the structure of a radiology information system relating to the exemplary embodiments.

Firstly, a configuration of a radiology information system 10 (which will be called "the RIS 10" below) will be described in reference to FIG. 1.

The RIS 10 is a system for managing information such as medical service appointments and diagnostic records in a radiology department and configures part of a hospital information system (HIS).

The RIS 10 includes plural image capture request terminals 12 (which will be called "the terminals 12" below), a radiology information system (RIS) server 14 and radiographic image capturing systems 18 (hereinafter, referred to as "capturing systems") installed in individual radiographic image capturing rooms (or operating rooms) in a hospital being connected to a hospital network 16 that is structured by a wired or wireless local area network (LAN). The RIS 10 serves as part of the hospital information system (HIS) that is disposed in the same hospital, and an HIS server (not shown) that manages the entire HIS is also connected to the hospital network 16.

The terminals 12 are devices for doctors or a radiologic technologist to input/browse diagnostic information and facility reservations, and requests to capture radiographic images or image capture reservations are also performed from the terminals 12. Each of the terminals 12 is configured by a personal computer equipped with a display device, and the terminals 12 are connected by the hospital network 16 to the RIS server 14 so as to be capable of communicating with each other.

The RIS server 14 receives the image capture requests from the terminals 12, manages radiographic image capture schedules in the image capturing systems 18, and includes a database 14A.

The database 14A includes information relating to a patient, such as attribute information (name, ID, sex, date of birth, age, blood type, weight, and the like) of the patient, medical history, consultation history, and radiographic images captured in the past, information relating to electronic cassettes 32 used in the capturing systems 18, such as ID numbers, types, sizes, sensitivities, image capture areas where the electronic cassettes 32 are useable, starting dates of use, and numbers of times used, and environment information representing the environment in which the electronic cassettes 32 are to be used to capture radiographic images, that is, the environment in which the electronic cassettes 32 are to be used (for example, an radiographic image capturing room or an operating room).

The image capturing systems 18 capture radiographic images by operation of the doctors or radiologic technologists in response to an instruction from the RIS server 14. Each of the capturing systems 18 is equipped with a radiation generator 34 that irradiates a subject with radiation X (see also FIG. 3) from a radiation source 130 (see also FIG. 7) of a radiation amount corresponding to image capture conditions, plural electronic cassettes 32A and 32B (two in the present embodiment) that includes a built-in radiation detector 60 (see also FIG. 5) that absorbs the radiation X that has been transmitted through an image capture area of the patient and generates charges, and generates image information (data) representing radiographic image information (data) based on the generated charge amount, a cradle 40 that charges a battery built into the electronic cassettes 32A and 32B, and a console 42 that controls the electronic cassettes 32A and 32B, the radiation generator 34, and the cradle 40. Since the electronic cassettes 32A and 32B have the same configuration, there are hereinafter referred simply to as "electronic cassettes 32" unless discrimination is not needed.

The console 42 obtains from the RIS server 14 various information stored in the database 14A, stores the information in a hard disk drive (HDD) 110 which will be described later (see also FIG. 7), and controls the electronic cassettes 32, the radiation generator 34, and the cradle 40 based on the information.

Figure 2:
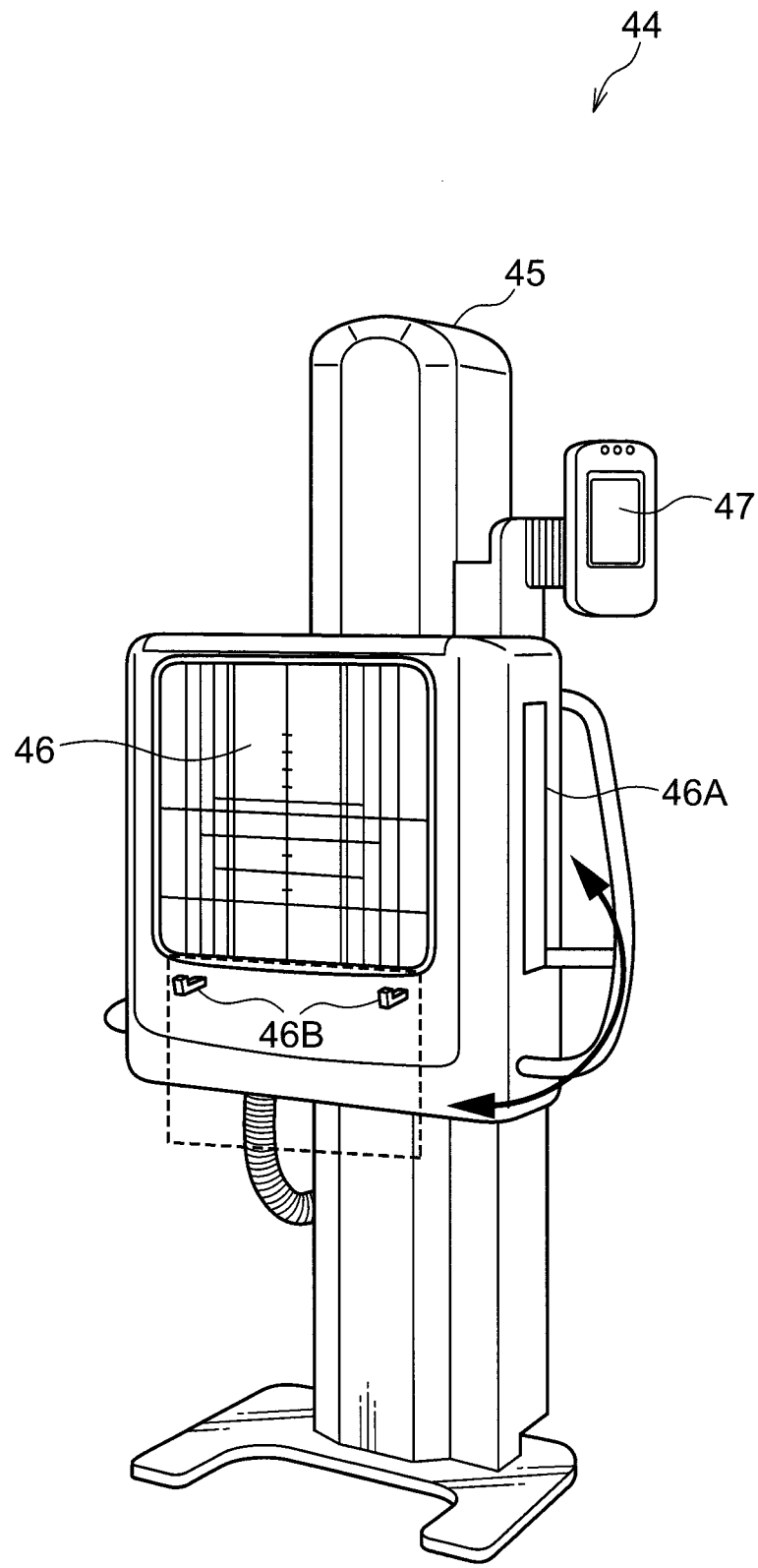
FIG. 2 is a side view showing an example of the state of an image capturing stand that is disposed in a radiographic image capturing room relating to the exemplary embodiments.
Figure 3:
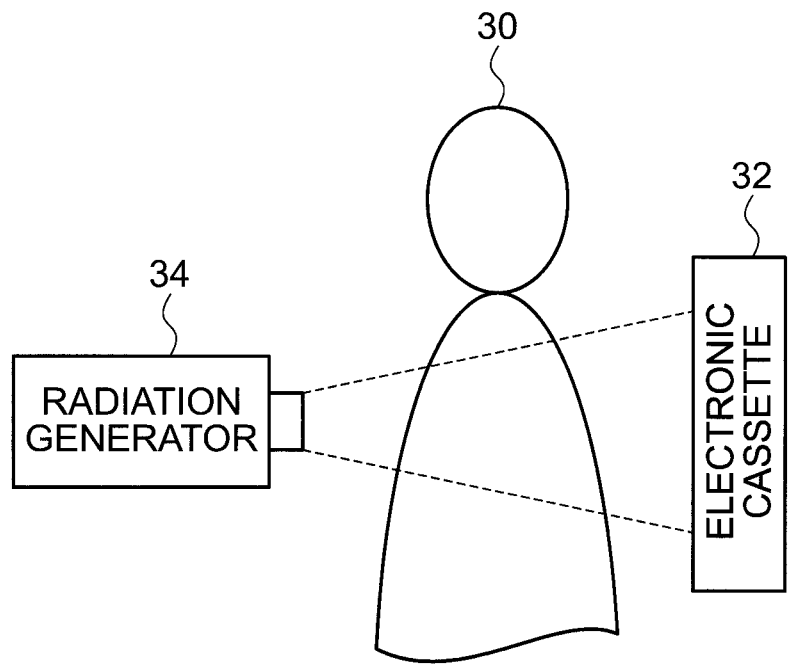
FIG. 3 is a schematic drawing showing the placement of an electronic cassette at a time of radiographic image capturing relating to the exemplary embodiments.

FIGS. 2 and 3 show examples of the arrangements of the image capturing systems 18 in an radiographic image capturing room 44 according to the present exemplary embodiment.

As shown in FIG. 2, an image capturing stand 45 for holding the electronic cassettes 32 at the time of carrying out radiographic image capturing in a standing state, is set in the radiographic image capturing room 44. The space in front of the image capturing stand 45 is the image capturing position for the patient at the time when radiographic image capturing is carried out in a standing state.

At the image capturing stand 45, an image capturing section 46 can be raised and lowered, and an operation panel 47 for raising and lowering the image capturing section 46 is provided. An accommodating portion 46A that can accommodate the electronic cassette 32 is provided in the image capturing section 46.

Due to the electronic cassette 32 being accommodated in the accommodating portion 46A of the image capturing section 46, the electronic cassette 32 is disposed such that there is an interval between the electronic cassette 32 and the radiation generator 34 at the time of capturing a radiographic image, as shown in FIG. 3. The region between the radiation generator 34 and the electronic cassette 32 at this time is an image capturing position at which a patient 30 is positioned. Capturing of a radiographic image is instructed, and the radiation generator 34 emits radiation of a radiation amount that corresponds to image capturing conditions and the like that have been given in advance. Due to radiation X, that is emitted from the radiation generator 34, passing through the patient 30 positioned at the image capturing position, the radiation X carries image information, and thereafter, is irradiated onto the electronic cassette 32.

Figure 4:
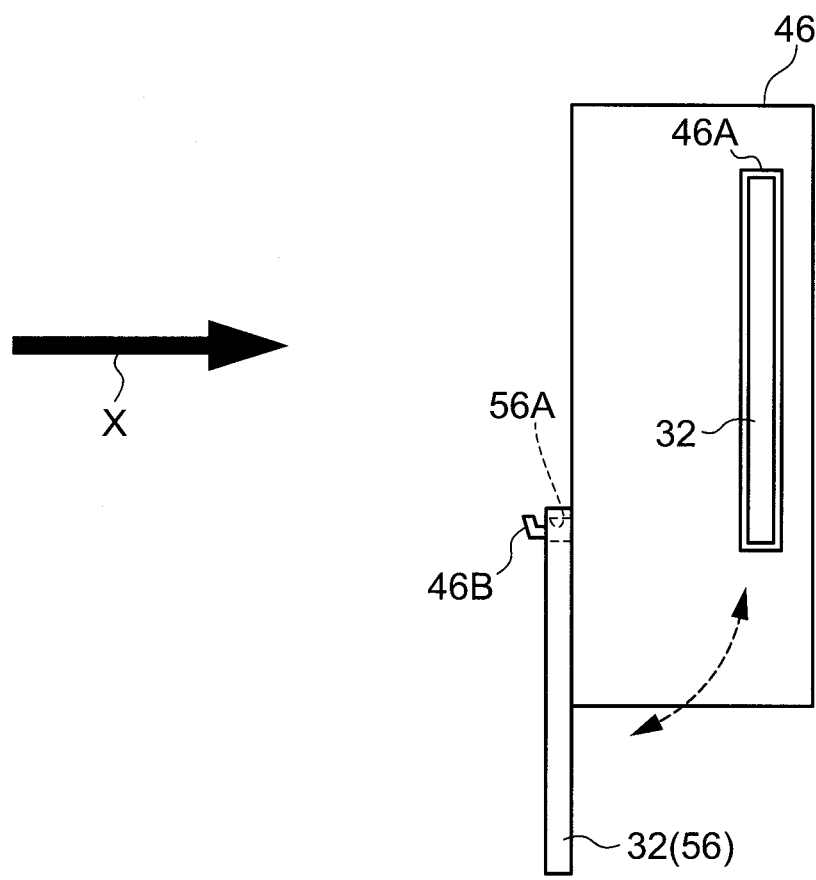
FIG. 4 is a schematic drawing showing the placement of electronic cassettes at the image capturing stand when capturing an elongated image relating to a first exemplary embodiment.

The image capturing system 18 can capture an elongated image by using two of the electronic cassettes 32. As shown in FIG. 2, a pair of hooks 46B for holding the electronic cassette 32 at the time of capturing an elongated image, is provided at the image capturing section 46. When capturing an elongated image, one electronic cassette 32 is accommodated in the accommodating portion 46A, and another electronic cassette 32 is engaged with the hooks 46B. As shown in FIG. 4, the hooks 46B are disposed at a position such that a portion of the lower side of the electronic cassette 32 accommodated in the accommodating portion 46A, and a portion of the upper side of the electronic cassette 32 engaged with the hooks 46B, overlap. Due thereto, the image that is captured by the electronic cassette 32 accommodated in the accommodating portion 46A, and the image that is captured by the electronic cassette 32 engaged with the hooks 46B, partially overlap.

Note that the electronic cassette 32 is not limited to being used only in a radiographic image capturing room or an operating room, and, due to the portability thereof can, for example, be used in medical examinations or in doctors' rounds within a hospital or the like as well.

Figure 5:
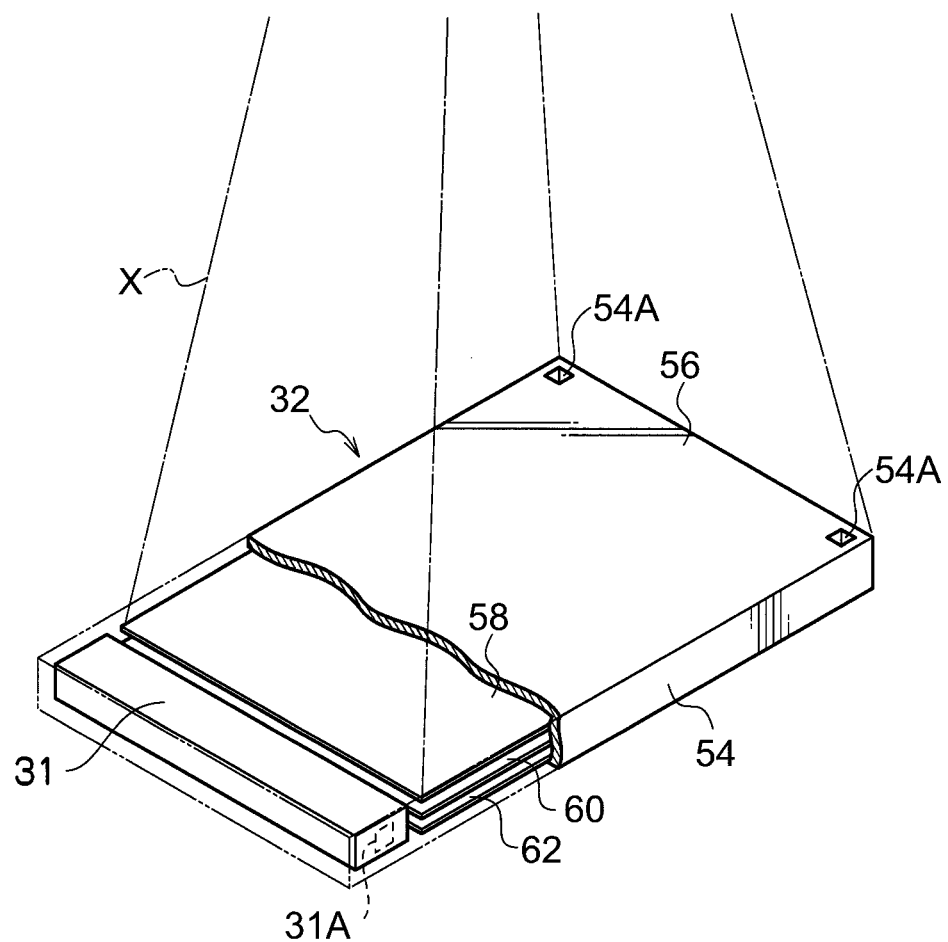
FIG. 5 is a transparent perspective view showing the internal structure of the electronic cassette relating to the first exemplary embodiment.

FIG. 5 shows the internal configuration of the electronic cassette 32 pertaining to the exemplary embodiment.

As shown in FIG. 5, the electronic cassette 32 is equipped with a casing 54 formed by a material that allows the radiation X to be transmitted therethrough, and the electronic cassette 32 is configured to have a waterproof and hermetic structure. There is the fear that blood or another contaminant may adhere to the electronic cassette 32 when the electronic cassette 32 is used in the operating room 44 or the like. Thus, the electronic cassette 32 is configured to have a waterproof and hermetic structure and is washed with an antiseptic as needed, so that one electronic cassette 32 can be used repeatedly.

A connection terminal 31A is provided at a side surface of the casing 54. Further, a pair of engaging holes 54A, that are for engaging with the hooks 46B of the image capturing section 46, are provided at one end portion in the longitudinal direction of the casing 54.

A grid 58 that removes the scattered radiation of the radiation X due to the patient, the radiation detector 60 that detects the radiation X that has been transmitted through the patient, and a lead plate 62 that absorbs the back-scattered radiation of the radiation X, are disposed within the casing 54 in that order from an irradiated surface 56 side of the casing 54 onto which the radiation X is irradiated. The irradiated surface 56 of the casing 54 may be structured as the grid 58.

A case 31, that accommodates electronic circuits including a microcomputer and accommodates a power source 96 that is chargeable, is disposed at the other end side of the interior of the casing 54. The radiation detector 60 and the aforementioned electronic circuits are operated by electric power that is supplied from the power source 96 disposed in the case 31. In order to avoid damage, that accompanies the irradiation of the radiation X, to the various types of circuits that are accommodated within the case 31, a lead plate or the like can be placed at the irradiated surface 56 side of the case 31.

Figure 6:
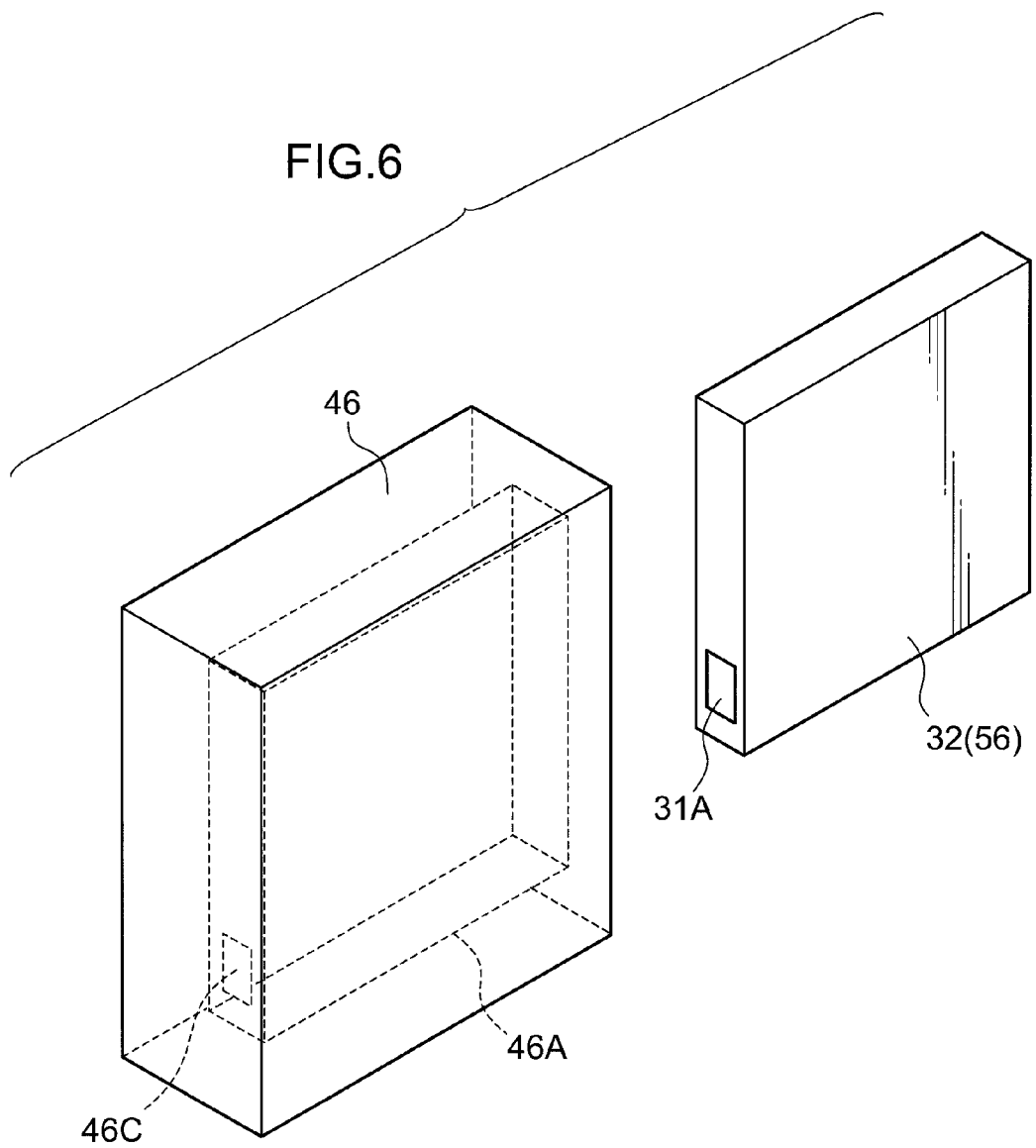
FIG. 6 is a transparent perspective view showing the structure of an accommodating portion of an image capturing section relating to the first exemplary embodiment.

As shown in FIG. 6, a connection terminal 46C is provided within the accommodating portion 46A of the image capturing section 46, at a position that corresponds to the connection terminal 31A when the electronic cassette 32 is accommodated. The connection terminal 46C contacts and can communicate with the connection terminal 31A when the electronic cassette 32 is accommodated in the accommodating portion 46A. The electronic cassette 32 accommodated in the accommodating portion 46A is connected to the console 42 via the connection terminal 31A and a communication cable 43A (see FIG. 7).

A communication cable 43B (see FIG. 7) is provided at the image capturing stand 45. When the electronic cassette 32 is engaged with the hooks 46B, the communication cable 43B is connected to the connection terminal 31A of that electronic cassette 32. The electronic cassette 32 that is engaged with the hooks 46B is connected to the console 42 via the communication cable 43B.

Figure 7:
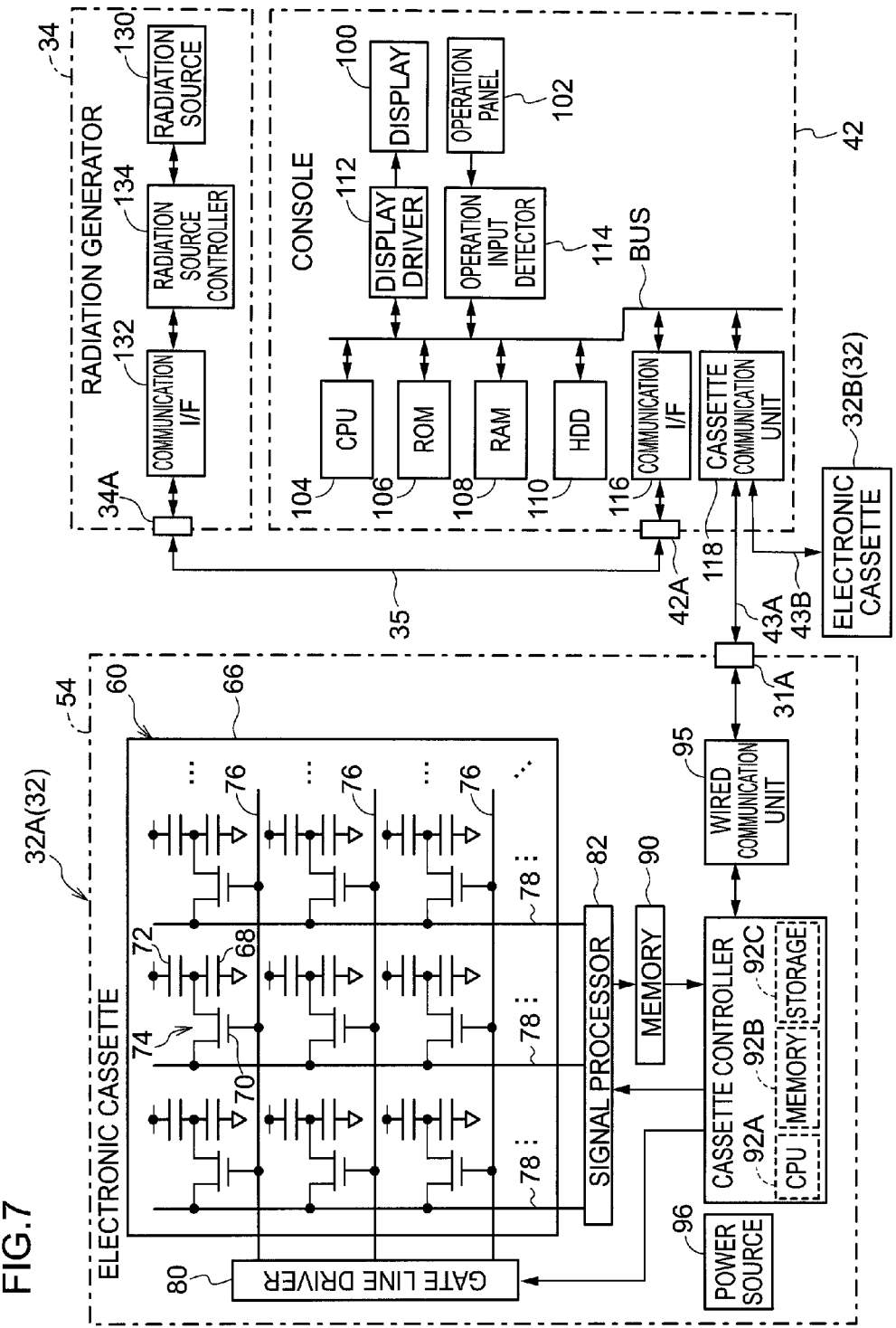
FIG. 7 is a block diagram showing the structure of main portions of an electrical system of a radiographic image capturing system relating to the first exemplary embodiment.

Next, the structure of main portions of the electrical system of the image capturing system 18 relating to the present exemplary embodiment is described with reference to FIG. 7. Note that FIG. 7 shows an example in which the electronic cassette 32A is connected to the communication cable 43A, and the electronic cassette 32B is connected to the communication cable 43B. Further, because the electronic cassettes 32A, 32B have the same structure, FIG. 7 illustrates the structure of the main portions of the electrical system of only the electronic cassette 32A.

As shown in FIG. 7, a connection terminal 34A for performing wired communication with the console 42 is disposed in the radiation generator 34. A connection terminal 42A for performing communication with the radiation generator 34 is disposed in the console 42. The connection terminal 34A of the radiation generator 34 and the connection terminal 42A of the console 40 are connected via a connection cable 35.

The radiation detector 60 built into the electronic cassette 32 is configured by a photoelectric conversion layer that absorbs and converts the radiation X into electric charges being layered on a TFT active matrix substrate 66. The photoelectric conversion layer is formed of, for example, amorphous selenium (a-Se) whose main component (e.g., having a content percentage equal to or greater than 50%) is selenium, and when the photoelectric conversion layer is irradiated with the radiation X, the photoelectric conversion layer converts the radiation X which has been irradiated into electric charges by generating, inside itself, electric charges (electron-hole pairs) of an electric charge amount corresponding to the amount of the radiation X which has been irradiated. The radiation detector 60 may also, instead of a material that directly converts the radiation X into electric charges such as amorphous selenium, use a fluorescent material and a photoelectric conversion element (photodiode) to indirectly convert the radiation X into electric charges. As the phosphor material, gadolinium oxysulfide (GOS) and cesium iodide (CsI) are well known. In this case, conversion of the radiation X into light is performed by the fluorescent material, and conversion of the light into electric charges is performed by the photodiode of the photoelectric conversion element.

Further, on the TFT active matrix substrate 66, numerous pixels 74 (in FIG. 7, the photoelectric conversion layer corresponding to the individual pixels 74 is schematically shown as photoelectric converters 72) equipped with storage capacitors 68 that store the electric charges that have been generated by the photoelectric conversion layer and TFTs 70 for reading the electric charges that have been stored in the storage capacitors 68 are arranged in a matrix. The electric charges that have been generated in the photoelectric conversion layer by the irradiation of the electronic cassette 32 with the radiation X are stored in the storage capacitors 68 of the individual pixels 74. Thus, the image information that had been carried in the radiation X with which the electronic cassette 32 was irradiated is converted into electric charge information (an amount of electric charge) and is held in the radiation detector 60.

Further, on the TFT active matrix substrate 66, there are disposed plural gate lines 76, which extend in a constant direction (row direction) and are for switching ON and OFF the TFTs 70 of the individual pixels 74, and plural data lines 78, which extend in a direction (column direction) orthogonal to the gate lines 76 and are for reading the stored electric charges from the storage capacitors 68 via the TFTs 70 that have been switched ON. The individual gate lines 76 are connected to a gate line driver 80, and the individual data lines 78 are connected to a signal processor 82. When the electric charges are stored in the storage capacitors 68 of the individual pixels 74, the TFTs 70 of the individual pixels 74 are switched ON in order in row units by signals that are supplied via the gate lines 76 from the gate line driver 80. The electric charges that are stored in the storage capacitors 68 of the pixels 74 whose TFTs 70 have been switched ON are transmitted through the data lines 78 as electric charge signals and are inputted to the signal processor 82. Consequently, the electric charges that are stored in the storage capacitors 68 of the individual pixels 74 are read in order in row units.

Figure 8:
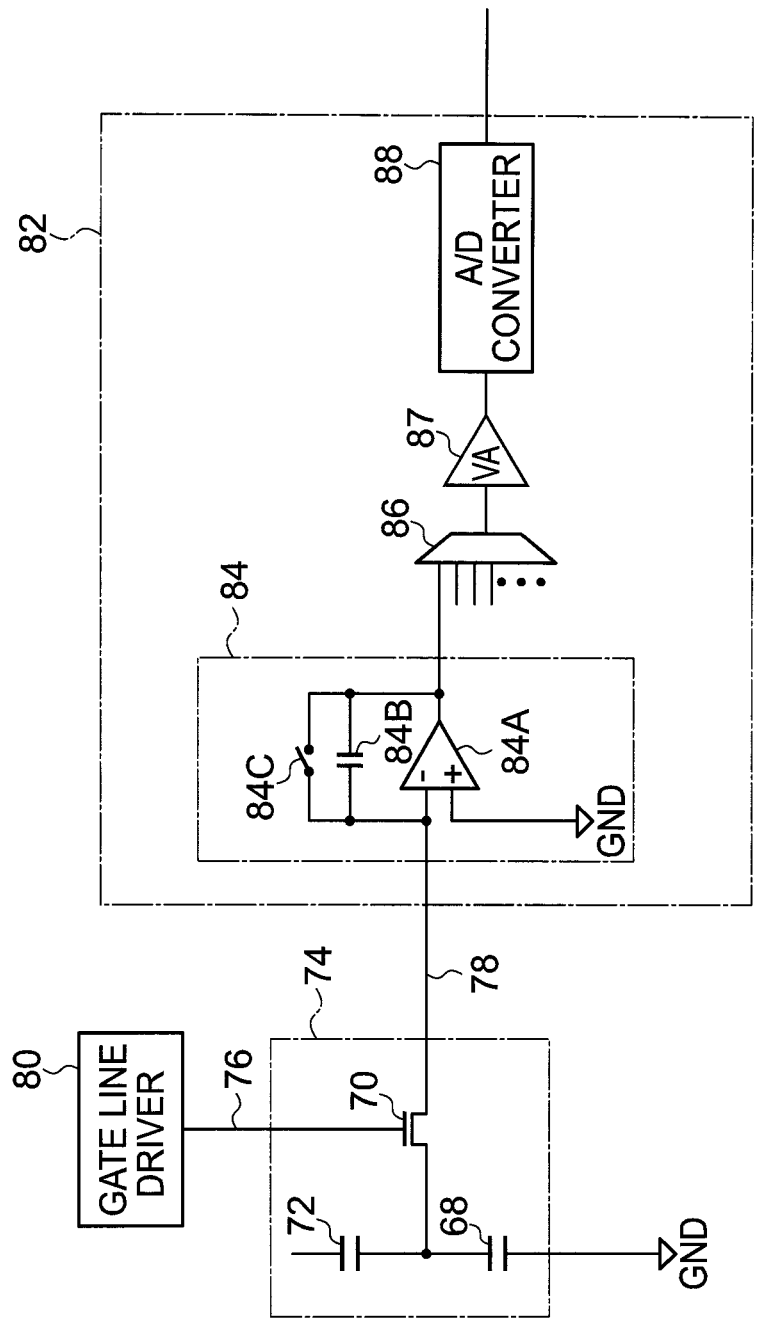
FIG. 8 is an equivalent circuit diagram focusing on one pixel of a radiation detector relating to the exemplary embodiments.

FIG. 8 shows an equivalent circuit diagram focusing on one pixel portion of the radiation detector 60 pertaining to the exemplary embodiment.

As shown in FIG. 8, a source of the TFT 70 is connected to the data line 78, and the data line 78 is connected to the signal processor 82. Further, a drain of the TFT 70 is connected to the storage capacitor 68 and to the photoelectric converter 72, and a gate of the TFT 70 is connected to the gate line 76.

The signal processor 82 is equipped with a sample/hold circuit 84 for each of the individual data lines 78. The electric charge signals that have been transmitted through the individual data lines 78 are held in the sample/hold circuits 84. The sample/hold circuit 84 includes an operational amplifier 84A and a capacitor 84B and converts the electric charge signal into an analog voltage. Further, a switch 84C, which serves as a reset circuit that causes both electrodes of the capacitor 84B to short to cause the electric charge stored in the capacitor 84B to be discharged as a result of the switch 84C being switched ON, is disposed in the sample/hold circuit 84.

A multiplexer 86 and an analog/digital (A/D) converter 88 are connected in this order at an output side of the sample/hold circuits 84. The electric charge signals held in the individual sample/hold circuits 84 are converted into analog voltages, and the analog voltages are inputted in order (serially) to the multiplexer 86 and converted into digital image data by the A/D converter 88.

A memory 90 is connected to the signal processor 82 (see FIG. 7). The image data that have been outputted from the A/D converter 88 of the signal processor 82 are stored in order (sequentially) in the memory 90. The memory 90 has a storage capacity that is capable of storing a predetermined number of frames' worth of image data representing a radiographic image, and each time reading of electric charges is performed one line at a time, the one line's worth of image data that have been read are sequentially stored in the memory 90.

The memory 90 is connected to a cassette controller 92 that controls operation of the entire electronic cassette 32. The cassette controller 92 is realized by a microcomputer, and includes a central processing unit (CPU) 92A, a memory 92B including ROMs and RAMs, and a non-volatile storage unit 92C formed by a HDD or a flash memory.

A wired communication unit 95 is connected to the cassette controller 92. The wired communication unit 95 is connected to the connection terminal 31A and controls the transmission of various types of information between the electronic cassette 32 and the console 42 via the connection terminal 31A.

Further, the power source 96 is disposed in the electronic cassette 32, and the various circuits and elements mentioned above (such as the gate line driver 80, the signal processor 82, the memory 90, the wired communication unit 95, and the microcomputer that functions as the cassette controller 92) are actuated by power supplied from the power source 96. The power source 96 is charged by electronic power supplied via the communication cable 43A in a case in which the communication cable 43A is connected to the connection terminal 31A. The power source 96 has a built-in battery (a rechargeable secondary battery) so as to not impair the portability of the electronic cassette 32, and the power source 96 supplies power to the various circuits and elements from the charged battery. Note that in FIG. 7, wiring connecting each of the circuits and elements with the power source 96 are not shown.

The console 42 is configured as a server computer and is equipped with a display 100, which displays operation menus and radiographic images that have been captured, and an operation panel 102, which includes plural keys and by which various types of information and operation instructions are inputted.

Further, the console 42 pertaining to the exemplary embodiment is equipped with a CPU 104 that controls operation of the entire device, a ROM 106 in which various programs including a control program are stored beforehand, a RAM 108 that temporarily stores various types of data, the HDD 110 that stores and maintains various types of data, a display driver 112 that controls the display of various types of information on the display 100, and an operation input detector 114 that detects states of operation with respect to the operation panel 102. Further, the console 42 includes a communication interface (I/F) 116 that is connected to the connection terminal 42A and transmits various types of information to and receives various types of information from the radiation generator 34 via the connection terminal 42A and the communication cable 35 such as later-described exposure conditions and state information of the radiation generator 34, and a cassette communication unit 118 that transmits various types of information to and receives various types of information from the electronic cassette 32 by radio communication such as image capture control data and image data.

The CPU 104, the ROM 106, the RAM 108, the HDD 110, the display driver 112, the operation input detector 114, the communication interface 116, and the cassette communication unit 118 are interconnected via a system bus BUS. Consequently, the CPU 104 can access the ROM 106, the RAM 108 and the HDD 110, can control the display of various types of information on the display 100 via the display driver 112, can control the transmission of various types of information to and the reception of various types of information from the radiation generator 34 via the communication interface 116, can control the transmission of various types of information to and the reception of various types of information from the electronic cassette 32 via the cassette communication unit 118. Further, the CPU 104 can grasp states of operation by a user with respect to the operation panel 102 via an operation input detector 114.

The radiation generator 34 is equipped with the radiation source 130 that outputs the radiation X, a communication interface 132 that transmits various types of information to and receives various types of information from the console 42 such as exposure conditions and state information of the radiation generator 34, and a radiation source controller 134 that controls the radiation source 130 on the basis of received exposure conditions.

The radiation source controller 134 is also realized by a microcomputer, stores the received exposure conditions. The exposure conditions received from the console includes information on X-ray tube voltage, X-ray tube current, irradiation period and the like. The radiation source controller 134 causes the radiation source 130 to radiate the radiation X on the basis of the received exposure conditions.

Next, an operation of the capturing system 18 according to the present exemplary embodiment will be described.

One of the terminals 12 (see FIG. 1) receives an image capture request from one of the doctors or radiologic technologists. In the image capture request, there are designated the environment in which the electronic cassette 32 is to be used, the date and time of image capture, the area of the patient of which an image is to be captured, the attitude of capturing, the tube voltage, and dose of the radiation irradiated.

The terminal 12 notifies the RIS server 14 of the content of the received image capture request. The RIS server 14 stores, in the database 14A, the content of the image capture request which has been notified by the terminals 12.

The console 42 accesses the RIS 14 to acquire the content of the image capture request and displays the content of the image capture request on the display 100.

The doctor or radiologic technologist initiates capture of a radiographic image on the basis of the content of the image capture request displayed on the display 100.

For example, in a case in which image capturing is carried out in a standing position at the image capturing stand 45 by using the one electronic cassette 32, the power source of the electronic cassette 32 is turned on, and the electronic cassette 32 is accommodated in the accommodating portion 46A of the image capturing stand 45.

Figure 9:
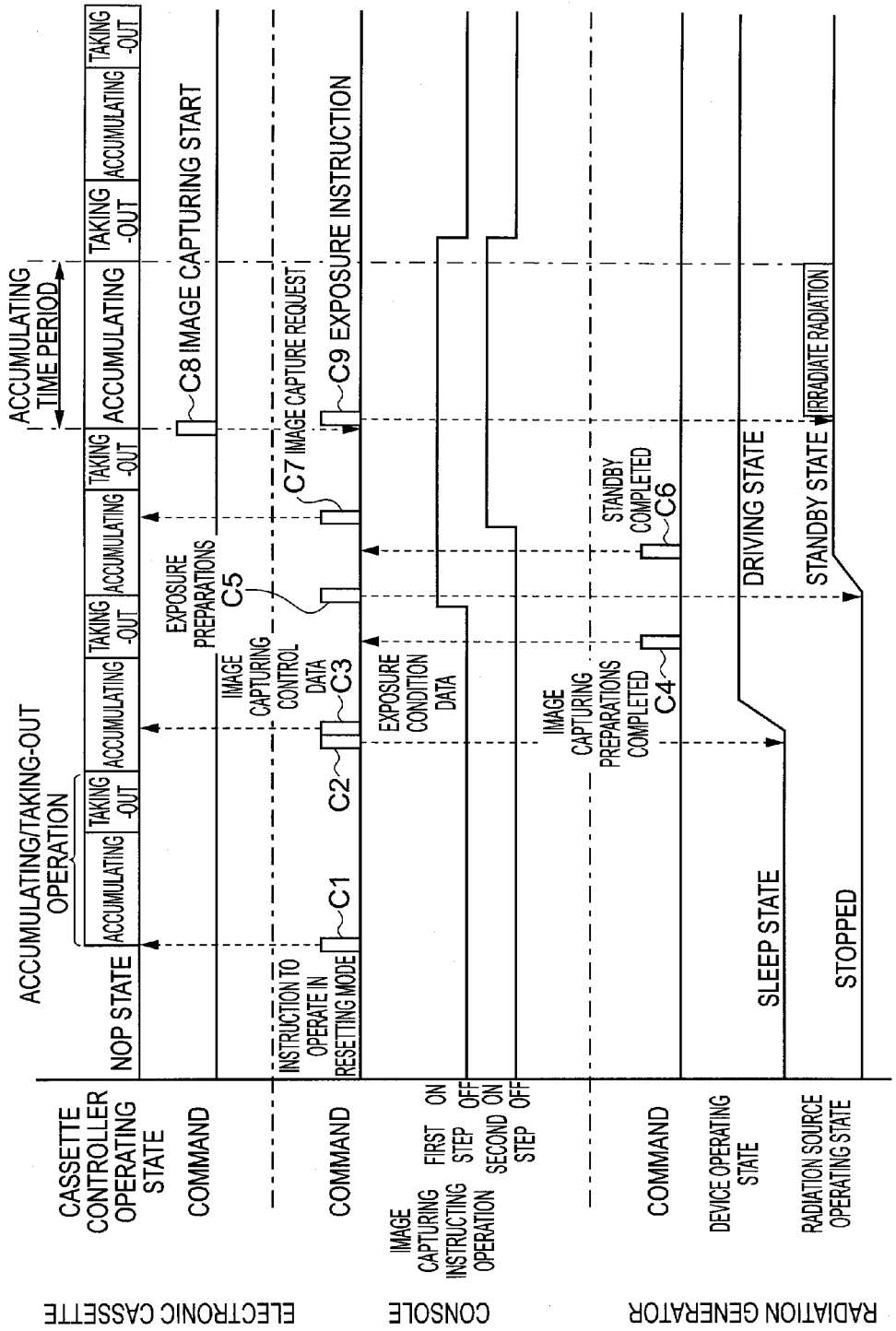
FIG. 9 is a timing chart showing the flow of operations at a time of capturing a radiographic image relating to the exemplary embodiments.

FIG. 9 shows a timing chart showing the flow of operations at the time of capturing a radiographic image by the image capturing system 18 relating to the first exemplary embodiment.

In the state in which the power source of the electronic cassette 32 is turned on (the start-up state), the operation mode is a non-operating state (NOP state) that is an initial state, and the electronic cassette 32 operates on the basis of instruction information (data) received from the console 42.

In a case in which the power source of the electronic cassette 32 is in an on state, the radiation detector 60 (see FIG. 7) incorporated within the electronic cassette 32 accumulates charges in the respective storage capacitors 68 due to dark current or the like, even if the radiation X is not being irradiated. Therefore, in a case in which the operation mode is the non-operating state, the cassette controller 92 is outputting an instruction signal that instructs resetting to the signal processor 82. At the signal processor 82, in response to an input of the instruction signal that instructs resetting, a switch 84C (see FIG. 8) is turned on, and both electrodes of a capacitor 84B are shorted. Due to both electrodes of the capacitor 84B being shorted in this way, the charges that are needlessly accumulated are discharged by the capacitor 84B.

After communication with the electronic cassette 32 becomes possible, the console 42 transmits, to the electronic cassette 32, instruction information (data) C1 that instructs operation in the resetting mode.

At the cassette controller 92, after the instruction information C1 that instructs operation in the resetting mode is received, the operation mode shifts to the resetting mode. After a predetermined accumulating time period elapses, the cassette controller 92 controls the gate line driver 80 to output ON signals to the respective gate lines 76 in order and line-by-line, and turns on the respective TFTs 36 that are connected to the respective gate lines 76 in order and line-by-line, and carries out taking-out of charges. Due thereto, the charges, that are accumulated in the respective storage capacitors 68, flow-out, in order and line-by-line, to the respective data lines 78 as charge signals. While the operation mode is the resetting mode, the cassette controller 92 repeats the accumulating/taking-out operation in which, after an accumulating time period elapses, ON signals are outputted to the respective gate lines 76 in order and line-by-line, the charges accumulated in the respective pixels 74 of the radiation detector 60 are taken-out, and resetting one frame.

After an exposure condition designating operation is carried out with respect to the operation panel 102, the console 42 transmits, to the radiation generator 34, exposure condition information (data) C2 such as the tube voltage, tube current, irradiation time period, and the like that are designated in the exposure condition designating operation. Further, the console 42 transmits, to the electronic cassette 32, image capturing control information (data) C3 such as the irradiation time period over which radiation is irradiated from the radiation generator 34, and the like at the time of capturing of a radiographic image.

At the radiation generator 34, after the power source is turned on and a predetermined initial start-up operation is completed, the operating state becomes a sleep state, and the radiation generator 34 stands-by (waits). After the exposure condition information C2 is received, the radiation generator 34 stores the received exposure condition information, and the operating state shifts to the driving state. After the operating state returns to the driving state, the radiation generator 34 transmits, to the console 42, information (data) C4 expressing completion of image capturing preparations.

After the image capturing control information C3 is received, the cassette controller 92 of the electronic cassette 32 stores the received image capturing control information.

After the information C4 expressing completion of image capturing preparations is received, the console 42 displays, on the display 100, the fact that image capturing preparations are completed, and an image capturing instructing operation that instructs image capturing becomes possible with respect to the operation panel 102. In the image capturing system 18 relating to the present exemplary embodiment, the image capturing instructing operation with respect to the operation panel 102 is a two-step operation. Image capturing of a radiographic image is carried out by carrying out the image capturing instructing operation of the second step after the image capturing instructing operation of the first step with respect to the operation panel 102. In this two-step image capturing instructing operation, for example, two buttons of the operation panel 102 may be depressed in order, or, for example, a single button may be depressed halfway and then fully depressed.

After the image capturing instructing operation of the first step is carried out on the operation panel 102, the console 42 transmits instruction information (data) C5, that instructs preparation for exposure, to the radiation generator 34.

After the instruction information C5 that instructs preparation for exposure is received, the radiation generator 34 carries out standby (preparation) of the radiation source 130 so that exposure will be carried out at the tube voltage and the tube current indicated by the exposure condition information that was stored immediately before. When standby of the radiation source 130 is completed, the radiation generator 34 transmits information (data) C6 that expresses completion of standby to the console 42.

After the console 42 receives the information C6 expressing completion of standby, the image capturing instructing operation of the second step becomes possible. After the image capturing instructing operation of the second step is carried out with respect to the operation panel 102, the console 42 transmits, to the electronic cassette 32, request information (data) C7 that requests permission to irradiate radiation for image capturing.

In response to the reception of the request information C7 that requests permission to irradiate radiation for image capturing, the cassette controller 92 carries out the accumulating/taking-out operation until the accumulating/taking-out operation of charges for one frame is completed. After the accumulating/taking-out operation of charges for one frame is completed, the cassette controller 92 transmits, to the console 42, instruction information (data) C8 that instructs starting of image capturing, and the operation mode shifts to the image capturing mode.

In response to the reception of the instruction information C8 that instructs starting of image capturing, the console 42 transmits instruction information (data) C9 that instructs exposure to the radiation generator 34.

In response to the reception of the instruction information C9 that instructs exposure, the radiation generator 34 causes the radiation X to be irradiated from the radiation source 130 for the irradiation time period expressed by the exposure condition information that was stored immediately before.

The radiation X irradiated from the radiation source 130 is transmitted through the patient 30, and thereafter, reaches the electronic cassette 32. Due thereto, charges, that correspond to the radiation amount of the irradiated radiation X, are accumulated in the storage capacitors 68 of the respective pixels 74 of the radiation detector 60 incorporated in the electronic cassette 32.

After transmitting the instruction information C8 that instructs starting of image capturing, the cassette controller 92 stands-by (waits) for the accumulating time period that is prescribed by the image capturing control information that was stored immediately before. Thereafter, the cassette controller 92 controls the gate line driver 80 to output ON signals to the respective gate lines 76 in order and line-by-line, and turns on the respective TFTs 36 connected to the respective gate lines 76 in order and line-by-line. Due thereto, the charges that are accumulated in the respective storage capacitors 68 flow-out to the respective data lines 78 as charge signals in order and line-by-line. The charge signals, that flow-out to the respective data lines 78, are inputted to the individual sample/hold circuits 84 and converted into voltage signals, and the converted voltage signals are inputted in order (serially) to the multiplexer, are converted into digital image data by the A/D converter, and are stored in the memory 90.

After image capturing ends, the cassette controller 92 transmits, to the console 42, the image data stored in the image memory 90. At the cassette controller 92, after the transfer of image data of one frame has finished, the operating mode shifts to the resetting mode. Here, it is assumed that continuous image capturing is not carried out and that the operation mode shifts to the resetting mode. However, continuous image capturing may be carried out.

The console 42 carries out various types of correcting image processings, such as shading correction and the like, on the received image data, and stores the image data after correction in the HDD 110. The image data stored in the HDD 110 is displayed on the display 100 for confirmation of the captured radiographic image, and is transferred to the RIS server 14 and stored in the RIS database as well. Due thereto, the captured radiographic image is displayed on the display of the terminal 12, and the doctor can carry out interpretation of the radiographic image, diagnosis, or the like.

As described above, the image capturing system 18 relating to the present exemplary embodiment can capture an elongated image by using two of the electronic cassettes 32. In a case in which an elongated image is captured by using two of the electronic cassettes 32 is to be carried out, the power sources of the two electronic cassettes 32 respectively are turned on. One of the two electronic cassettes 32 is accommodated in the accommodating portion 46A of the image capturing stand 45. The communication cable 43B is connected to the other electronic cassette 32, and this other electronic cassette 32 is engaged with the hooks 46B of the image capturing stand 45.

Also in a case in which capturing of an elongated image is carried out, as shown in FIG. 9, the console 42 transmits the instruction information C1, the image capturing control information C3, and the request information C7 to the respective electronic cassettes 32, and carries out image capturing.

Figure 10:
FIG. 10 is a timing chart showing operation timings of accumulating/taking-out operations of two electronic cassettes relating to the exemplary embodiments.

Because the electronic cassettes 32A, 32B respectively are repeatedly carrying out the accumulating/taking-out operation of charges, there are cases in which the image capturing timings are not synchronous as shown in FIG. 10.

Thus, in a case in which the two electronic cassettes 32 are connected, the console 42 carries out a synchronous control processing that synchronizes the accumulating/taking-out operations of the respective electronic cassettes 32.

Figure 11:
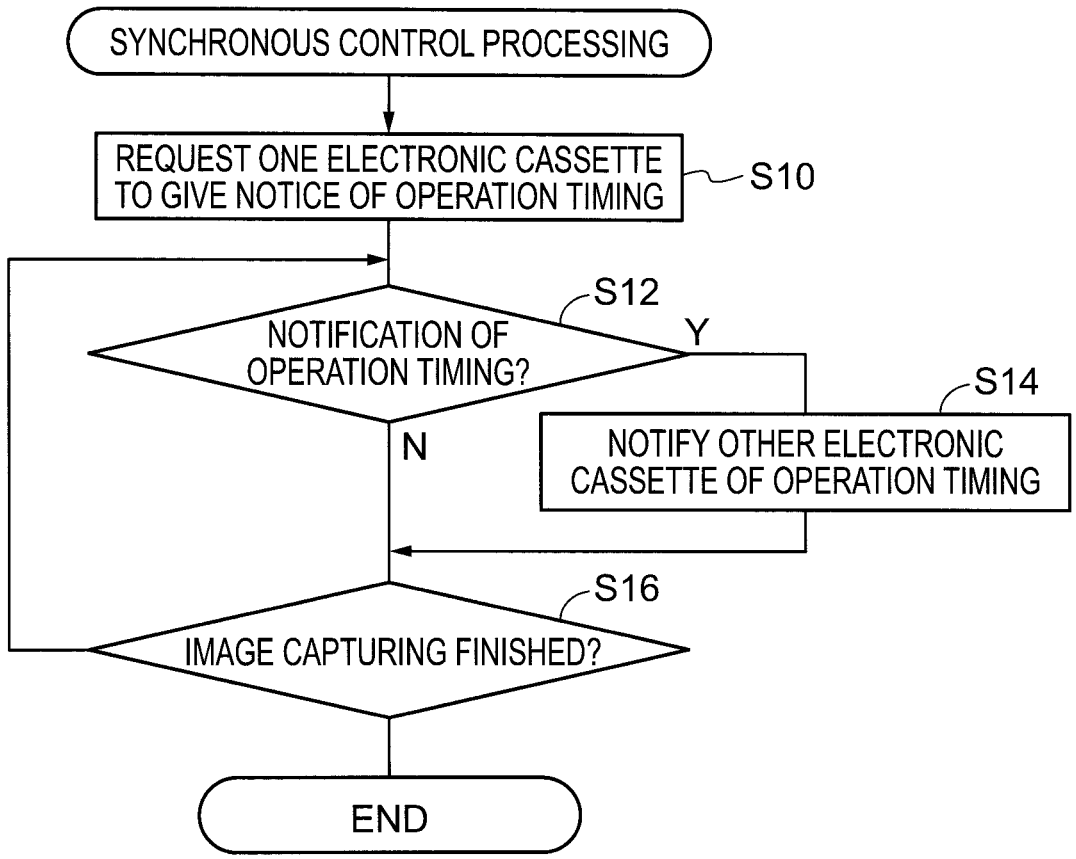
FIG. 11 is a flowchart showing the flow of a synchronous control processing program relating to the first exemplary embodiment.

The flow of the synchronous control processing that is executed by the CPU 104 is shown in FIG. 11.

In step S10, notification of the operation timing of the accumulating/taking-out operation is requested from one of the two electronic cassettes 32 (the electronic cassette 32A in the present exemplary embodiment).

The cassette controller 92 of the electronic cassette 32A notifies the console 42 of the start timing of the accumulating/taking-out operation of one frame, as the operation timing.

In step S12, judgment is made as to whether or not notification of the operation timing has been given. If the judgment is affirmative, the routine moves on to step S14. If the judgment is negative, the routine moves on to step S16.

In step S14, the CPU 104 of the console 42 notifies the other of the two electronic cassettes 32 (in the present exemplary embodiment, the electronic cassette 32B) of the operation timing of the one electronic cassette 32A.

At each notified operation timing, the cassette controller 92 of the electronic cassette 32B carries out the accumulating/taking-out operation that takes-out the charges after the accumulating time period elapses.

In step S16, judgment is made as to whether or not an image capturing instructing operation to end image capturing has been carried out with respect to the operation panel 102. If the judgment is affirmative, the synchronous control processing ends. If the judgment is negative, the routine moves on to step S12.

Figure 12:
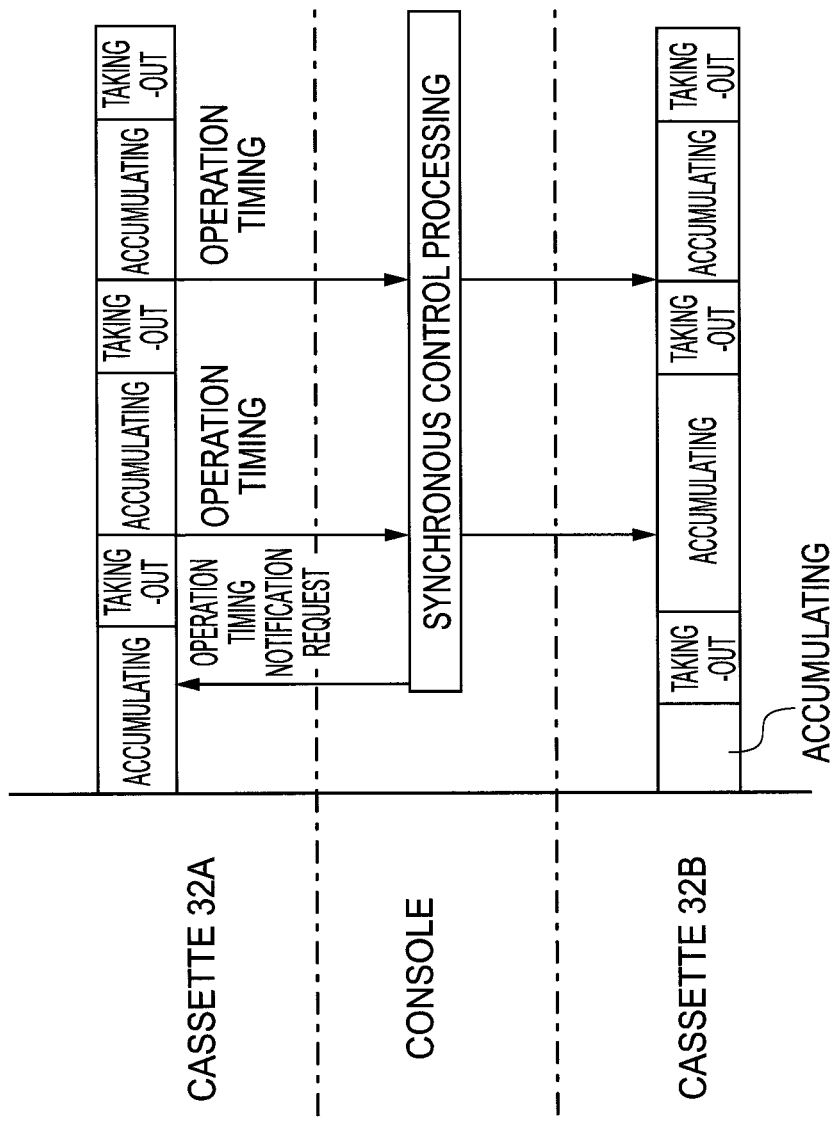
FIG. 12 is a timing chart showing changes in operation timings of accumulating/taking-out operations of two electronic cassettes in accordance with the synchronous control processing relating to the first exemplary embodiment.

In this way, the accumulating/taking-out operations of the two electronic cassettes 32 are carried out synchronously as shown in FIG. 12.

In a case in which capturing of an elongated image is to be carried out, in a case in which the console 42 receives the instruction information C8 from the respective electronic cassettes 32, the console 42 may transmit, to the radiation generator 34, the instruction information C9 instructing exposure. Or, because the accumulating/taking-out operations of the two electronic cassettes 32 are synchronous, the console 42 may transmit the instruction information C9 instructing exposure to the radiation generator 34 in a case in which the console 42 receives the instruction information C8 from the electronic cassette 32A that has provided notice of the operation timing.

After image capturing is finished, the cassette controllers 92 of the respective electronic cassettes 32 respectively transmit the respective image data stored in the image memories 90 to the console 42.

The console 42 carries out predetermined image processings on the image data of one frame that are respectively received, and combines the two images so as to generate image data expressing an elongated image.

The combining of the two captured images may be carried out by detecting in advance the ranges of overlapping regions in the two images respectively captured at the two electronic cassettes 32, and storing data expressing the two overlapping regions in the HDD 110 or the like, and combining the image data such that the overlapping regions overlap. Alternatively, as disclosed in JP-A No. 2002-85392, the image signal values of the respective images may be analyzed, and the connection state of the plural images may be recognized and the images combined. Or, as disclosed in JP-A No. 2005-257634, reference marks may be recorded in advance on regions that do not affect the respective images, and, in a case in which the combining processing is carried out, the images may be combined such that reference marks of the respective images coincide. The console 42 stores the generated image data after the image processings in the HDD 110 in a state of being associated with the patient information of the patient 30. The image data stored in the HDD 110 is displayed on the display 100 in order to confirm the captured radiographic images, or the like, and is transmitted to the RIS server 14 and stored in the RIS database as well.

As described above, in accordance with the present exemplary embodiment, by synchronizing the accumulating/taking-out operations of the respective electronic cassettes 32, the capturing of radiographic images at the plural electronic cassettes 32 can be carried out simultaneously. Due thereto, the capturing of an elongated image by using the plural electronic cassettes 32 also is possible.

Second Exemplary Embodiment

A second exemplary embodiment of the present invention is described next.

Because the structure of the radiographic information system 10 relating to the second exemplary embodiment is the same as that of the above-described first exemplary embodiment (see FIGS. 1 through 4, and FIGS. 6 and 7), description thereof is omitted here.

Figure 13:
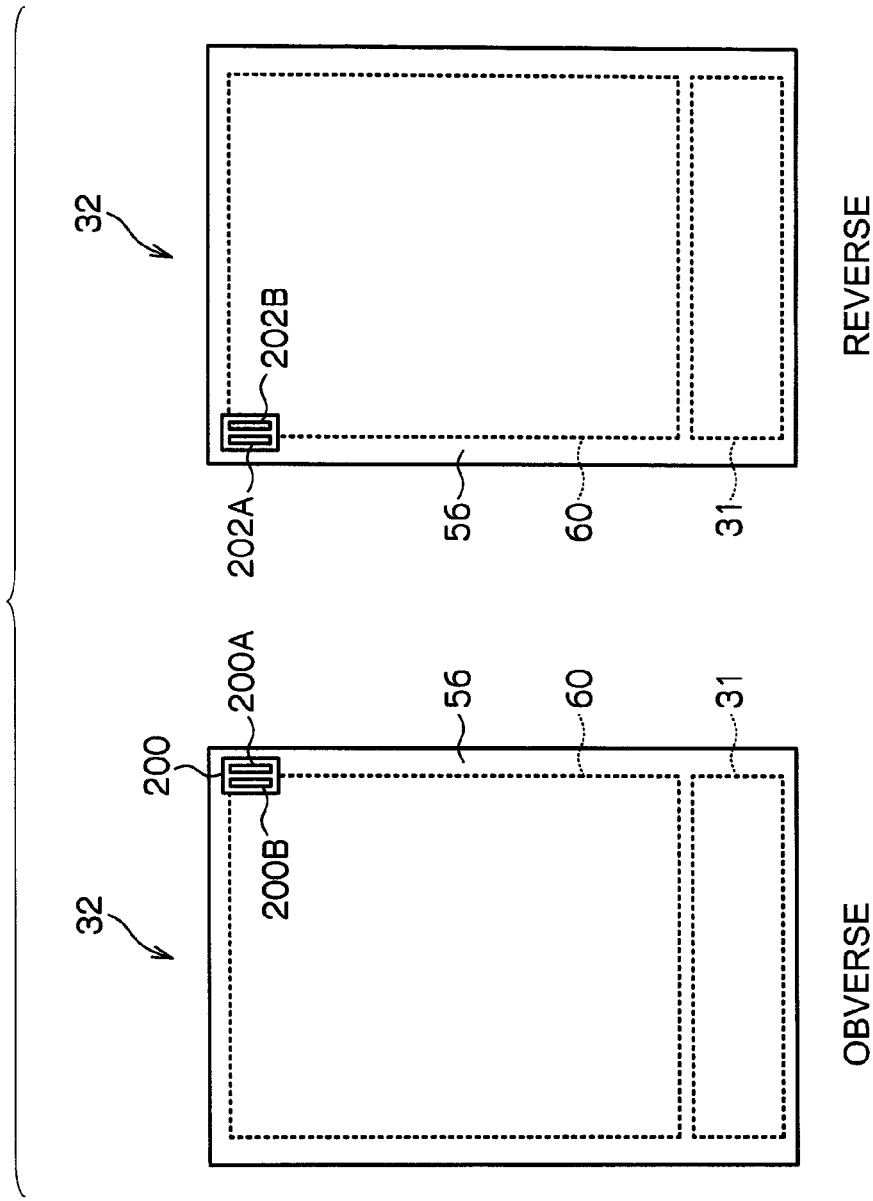
FIG. 13 is a plan view showing the structure of an electronic cassette relating to a second exemplary embodiment.

The structure of the electronic cassette 32 relating to the second exemplary embodiment is shown in FIG. 13. Note that the same portions as in the above first exemplary embodiment (FIG. 5) are denoted by the same reference numerals, and description thereof is omitted.

At the electronic cassette 32 relating to the second exemplary embodiment, an optical communication portion 200 is provided at an end portion of one side of the irradiated surface 56 of the casing 54 onto which the radiation is irradiated, and an optical communication portion 202 is provided at the end portion of the other side of a reverse 57 of the irradiated surface 56.

The optical communication portion 200 is provided with a light-emitting portion 200A that emits infrared light, and a light-receiving portion 200B that receives infrared light. The light-emitting portion 200A is provided further toward the outer side than the light-receiving portion 200B. The optical communication portion 202 is provided with a light-emitting portion 202A that emits infrared light and a light-receiving portion 202B that receives infrared light. The light-emitting portion 202A is provided further toward the outer side than the light-receiving portion 202B.

Figure 14:
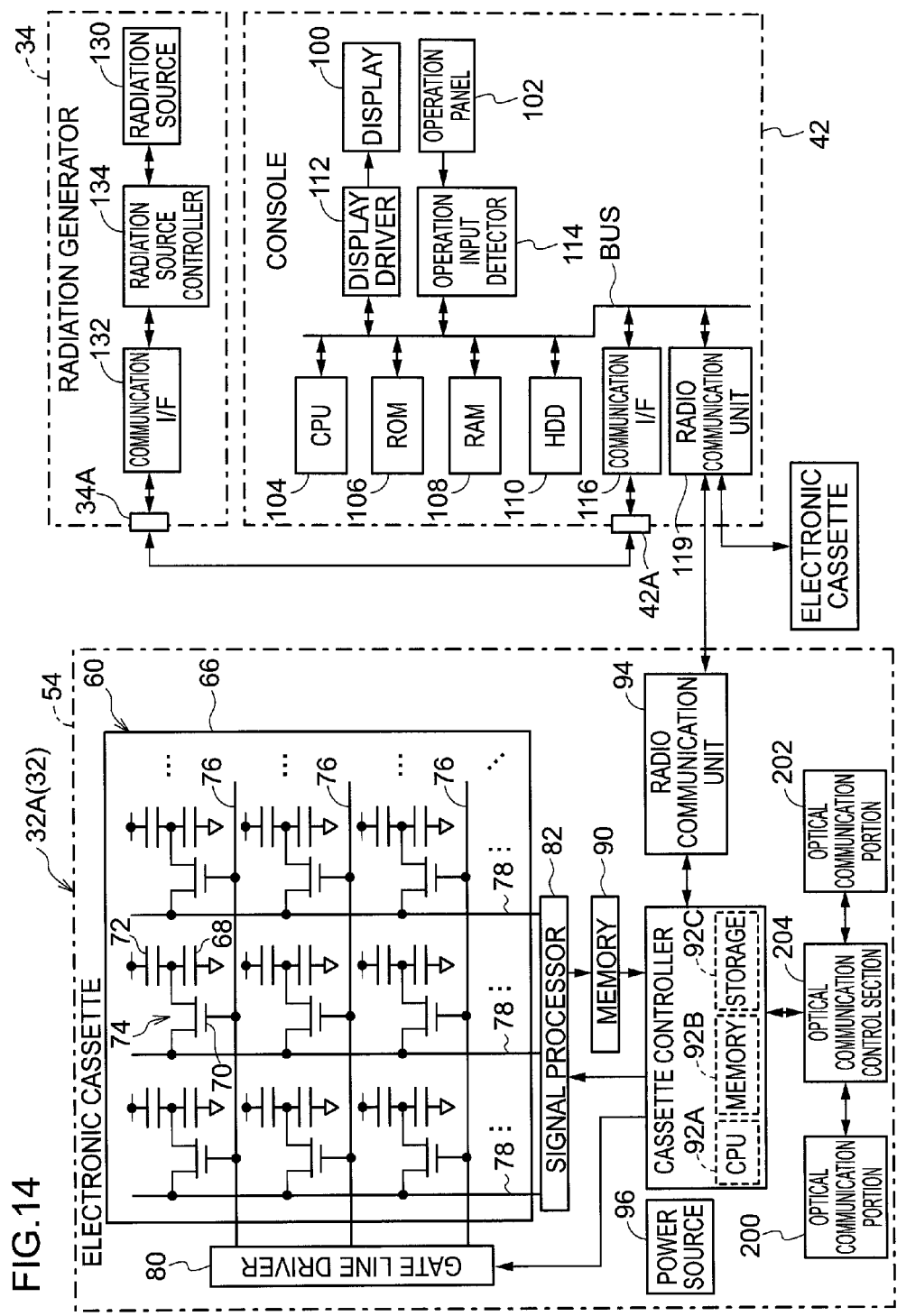
FIG. 14 is a block diagram showing the structure of main portions of an electrical system of a radiographic image capturing system relating to the second exemplary embodiment.

The structure of main portions of the electrical system of the image capturing system 18 relating to the second exemplary embodiment is described with reference to FIG. 14. Note that portions that are the same as those of the above-described first exemplary embodiment (FIG. 7) are denoted by the same reference numerals, and description thereof is omitted.

The optical communication portion 200 and the optical communication portion 202 are connected to an optical communication control section 204. The optical communication control section 204 carries out optical communication by controlling the optical communication portion 200 and the optical communication portion 202 respectively. The optical communication control section 204 is connected to the cassette controller 92. The cassette controller 92 can carry out optical communication with the other electronic cassettes 32 via the optical communication control section 204.

A radio communication unit 94 is connected to the cassette controller 92. The radio communication unit 94 corresponds to wireless Local Area Network (LAN) standards exemplified by Institute of Electrical and Electronics Engineers (IEEE) 802.11a/b/g or the like. The radio communication unit 94 controls the transfer of various types of information to and from external devices by radio communication. The cassette controller 92 can communicate by radio with the console 42 via the radio communication unit 94, and can transmit and receive various types of information to and from the console 42.

On the other hand, the console 42 has a radio communication unit 119 that can carry out transfer and receipt of various types of information, such as image capturing control information, image data and the like, by radio communication to and from the respective electronic cassettes 32. The radio communication unit 119 is connected to a system BUS. Accordingly, the CPU 104 can control the transfer and receipt of various types of information to and from the respective electronic cassettes 32 via the radio communication unit 119.

Namely, the image capturing system 18 relating to the present exemplary embodiment carries out transmission and reception of various types of information by radio communication between the electronic cassettes 32 and the console 42.

Figure 15:
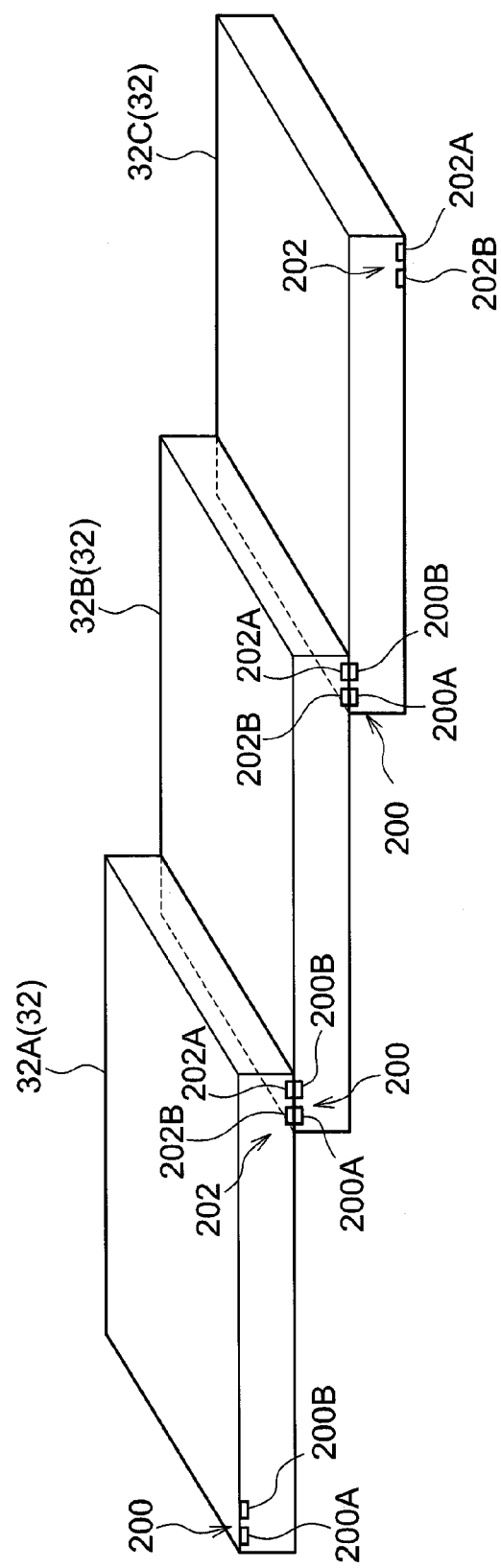
FIG. 15 is a perspective view showing the placement of electronic cassettes when capturing an elongated image relating to the second exemplary embodiment.

At the image capturing system 18 relating to the present exemplary embodiment, in a case in which an elongated image is to be captured, as shown in FIG. 15, the electronic cassettes 32 are overlapped such that the optical communication portions 200 of the irradiated surfaces 56 oppose the optical communication portions 202 of the reverses 57. FIG. 15 illustrates a case in which capturing of an elongated image is carried out by using three of the electronic cassettes 32 (32A through 32C).

Figure 16:
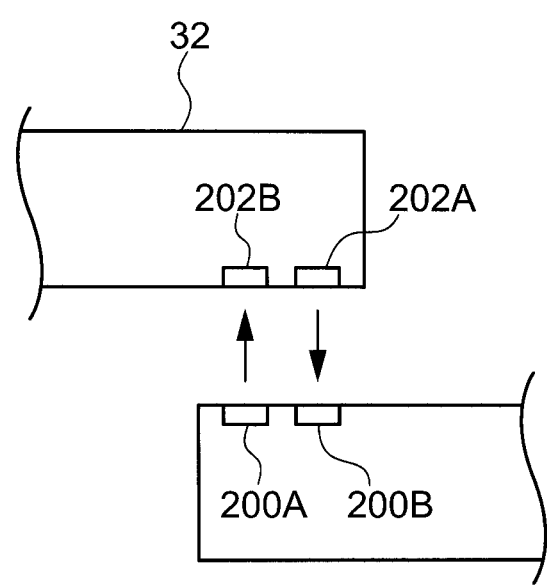
FIG. 16 is a perspective view showing the placed state at the time of carrying out optical communication between the electronic cassettes relating to the second exemplary embodiment.

In this case, as shown in FIG. 16, the respective electronic cassettes 32 are overlapped such that the lights of the light-emitting portions 200A of the optical communication portions 200 are received at the light-receiving portions 202B of the optical communication portions 202, and the lights of the light-emitting portions 202A of the optical communication portions 202 are received at the light-receiving portions 200B of the optical communication portions 200.

By overlapping the electronic cassettes 32 in this way, optical communication between the overlapped electronic cassettes 32 is possible.

Further, at the electronic cassette 32 relating to the present exemplary embodiment, the light-emitting portions 200A and 202A of the optical communication portions 200 and 202 are provided further toward the outer side than the light-receiving portions 200B and 202B. The effects of exterior noise on the light-receiving portion 200B and the light-receiving portion 202B can thereby be decreased.

In a case in which the electronic cassettes 32 are overlapped, it is easy for offset to arise in the overlapped positions due to shocks or the like, and therefore, the electronic cassettes 32 may be fixed by connecting members.

At the console 42, in a case in which capturing of an elongated image is to be carried out, as shown in FIG. 9, the instruction information C1, the image capturing control information C3, and the request information C7 are transmitted to the respective electronic cassettes 32 by radio communication, and image capturing is carried out.

Because the electronic cassettes 32A through 32C respectively are repeatedly carrying out the accumulating/taking-out operation, there are cases in which the image capturing timings are not synchronous.

Thus, on the basis of the connected states of the optical communication portions 200 and the optical communication portions 202, the respective electronic cassettes 32 relating to the present exemplary embodiment detect the above/below relationships of the overlapping and the order of the overlapping of the respective electronic cassettes 32. On the basis of the results of detection, the electronic cassettes 32 carry out synchronous control processing that synchronizes the accumulating/taking-out operations of the respective electronic cassettes 32.

Figure 17:
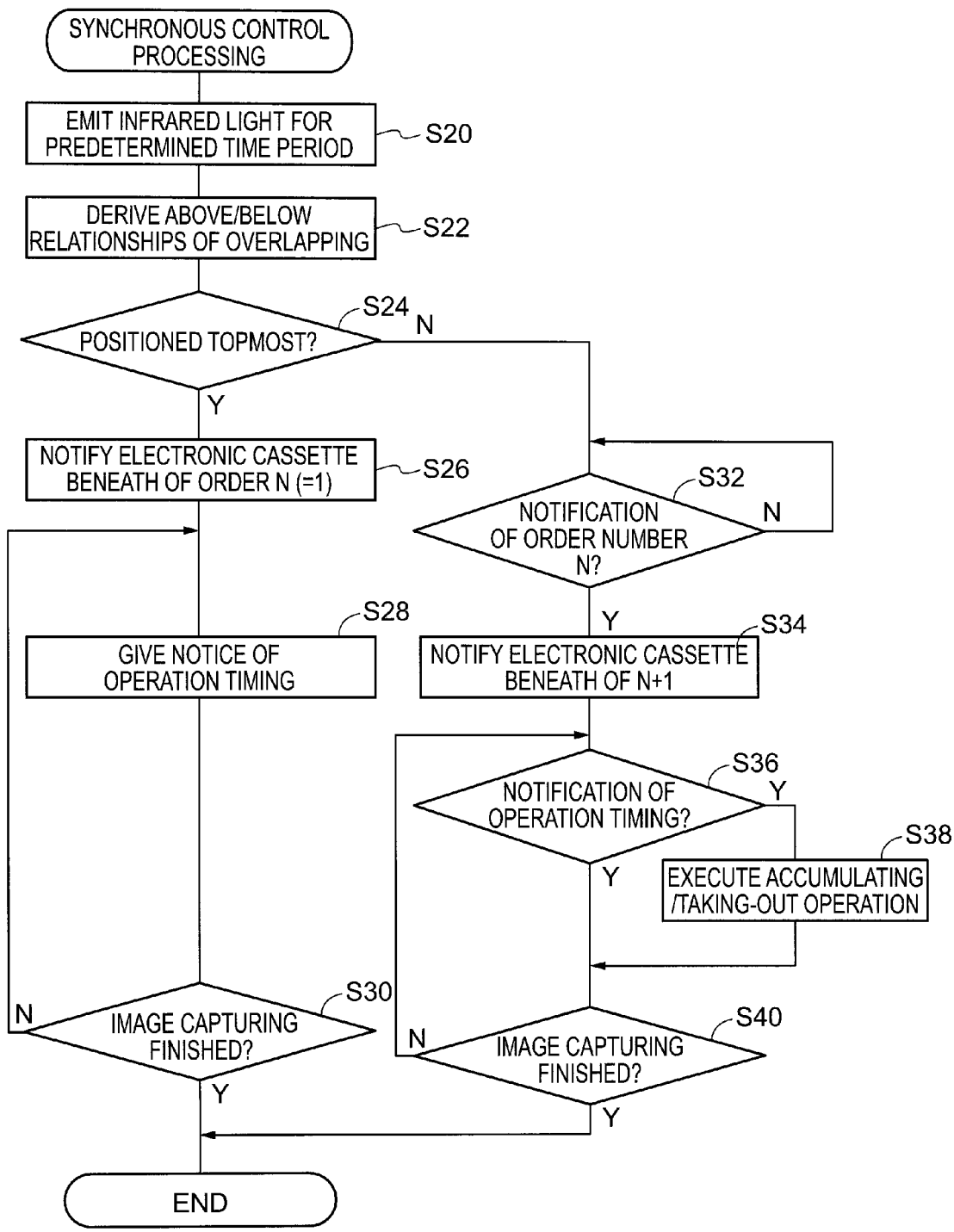
FIG. 17 is a flowchart showing the flow of a synchronous control processing program relating to the second exemplary embodiment.

FIG. 17 shows the flow of the synchronous control processing that is executed by the CPU 92A of the cassette controller 92 of the electronic cassette 32 in a case in which the image capturing control information C3 is received.

In step S20, infrared lights are emitted for a predetermined time period from the light-emitting portion 200A of the optical communication portion 200 and the light-emitting portion 202A of the optical communication portion 202.

In next step S22, the above/below relationships of the overlapping of the electronic cassettes 32 are derived on the basis of the results of detection of the infrared lights at the light-receiving portion 200B of the optical communication portion 200 and the light-receiving portion 202B of the optical communication portion 202. Namely, if infrared light is not detected at the light-receiving portion 200B, there is no electronic cassette 32 that is overlapped on the irradiated surface 56 side of the electronic cassette 32. If infrared light is detected at the light-receiving portion 200B, there is the electronic cassette 32 that is overlapped on the irradiated surface 56 side of the electronic cassette 32. Similarly, if infrared light is not detected at the light-receiving portion 202B, there is no electronic cassette 32 that is overlapped on the reverse 57 side of the electronic cassette 32. If infrared light is detected at the light-receiving portion 202B, there is the electronic cassette 32 that is overlapped on the reverse 57 side of the electronic cassette 32.

Due thereto, for example, if the three electronic cassettes 32A through 32C are overlapped as shown in FIG. 15, it is determined that the electronic cassette 32A is positioned topmost.

In next step S24, a judgment is made as to whether or not, in the above/below relationships determined in above step S22, the electronic cassette 32 is positioned topmost. If the judgment is affirmative, the routine moves on to step S26, whereas if the judgment is negative, the routine moves on to step S32.

In step S26, because the electronic cassette 32 is at the topmost position, an overlapping order N thereof is specified as 1. In order to carry out determination of the order N at the electronic cassette 32 that is overlapped therebeneath, the light-emitting portion 202A of the optical communication portion 202 is made to emit light, and the electronic cassette 32 therebeneath is notified of the order N.

In next step S28, at each start timing of the accumulating/taking-out operation of one frame, the light-emitting portion 202A of the optical communication portion 202 is made to emit light, and gives notice of the operation timing.

In next step S30, a judgment is made as to whether or not finishing of image capturing has been instructed from the console 42. If the judgment is affirmative, the synchronous control processing ends. If the judgment is negative, the routine moves on to step S26.

On the other hand, in step S32, the electronic cassette 32 awaits notification of the order N to the light-receiving portion 200B of the optical communication unit 200, from the electronic cassette 32 that is overlapped thereabove.

In step S34, an added value (N+1), that is obtained by adding one to the notified order N, is specified as the order N of its own. Then, the light-emitting portion 202A of the optical communication portion 202 emits light, and notifies the electronic cassette 32 therebeneath of the own order N, i.e., value obtained by adding one to the notified N.

Due thereto, for example, in a case in which the three electronic cassettes 32A through 32C are superposed as shown in FIG. 15, the electronic cassette 32A is determined to have order N=1, the electronic cassette 32B is determined to have order N=2, and the electronic cassette 32C is determined to have order N=3.

In next step S36, a judgment is made as to whether or not the operation timing has been notified from the electronic cassette 32 thereabove. If the judgment is affirmative, the routine moves on to step S38. If the judgment is negative, the routine moves on to step S40.

In step S36, at each operation timing that is notified, the accumulating/taking-out operation is started.

In step S40, a judgment is made as to whether or not finishing of image capturing has been instructed from the console 42. If the judgment is affirmative, the synchronous control processing ends. If the judgment is negative, the routine moves on to step S36.

Due thereto, the accumulating/taking-out operations of the three electronic cassettes 32A through 32C are carried out synchronously.

In a case in which capturing of an elongated image is to be carried out, in the same way as in the first exemplary embodiment, in a case in which the console 42 receives the instruction information C8 from the respective electronic cassettes 32, the console 42 may transmit, to the radiation generator 34, the instruction information C9 instructing exposure. Alternatively, because the accumulating/taking-out operations of the three electronic cassettes 32A through 32C are synchronous, the console 42 may transmit the instruction information C9 instructing exposure to the radiation generator 34 in a case in which the console 42 receives the instruction information C8 from the electronic cassette 32A.

After image capturing is finished, the cassette controllers 92 of the respective electronic cassettes 32 respectively transmit the respective image data stored in the image memories 90 to the console 42 by radio communication.

The console 42 carries out predetermined image processings on the image data of one frame that are respectively received, and combines the three images so as to generate image data expressing an elongated image.

Note that, in the image capturing system 18 relating to the second exemplary embodiment, because the electronic cassettes 32 are made to overlap one another, there are cases in which offset in the overlapped areas of the overlapping arises. Thus, the electronic cassettes 32 may, on the basis of the connected states of the optical communication portions 200 and the optical communication portions 202, determine overlapping amounts and notify the console 42 of the overlapping areas, and the console 42 may combine the images on the basis of the overlapping areas.

As described above, in accordance with the present exemplary embodiment, by carrying out communication among the electronic cassettes 32 and synchronizing the cycles of the accumulating/taking-out operations of the other electronic cassettes 32 with the cycle of the accumulating/taking-out operation of any one of the electronic cassettes 32, the capturing of radiographic images at the plural electronic cassettes 32 can be carried out simultaneously.

Third Exemplary Embodiment

A third exemplary embodiment of the present invention is described next.

Because the structure of the radiographic information system 10 and the internal structure of the electronic cassette 32 relating to the third exemplary embodiment are the same as those of the above-described first exemplary embodiment (see FIGS. 1 through 8), description thereof is omitted here.

Figure 18:
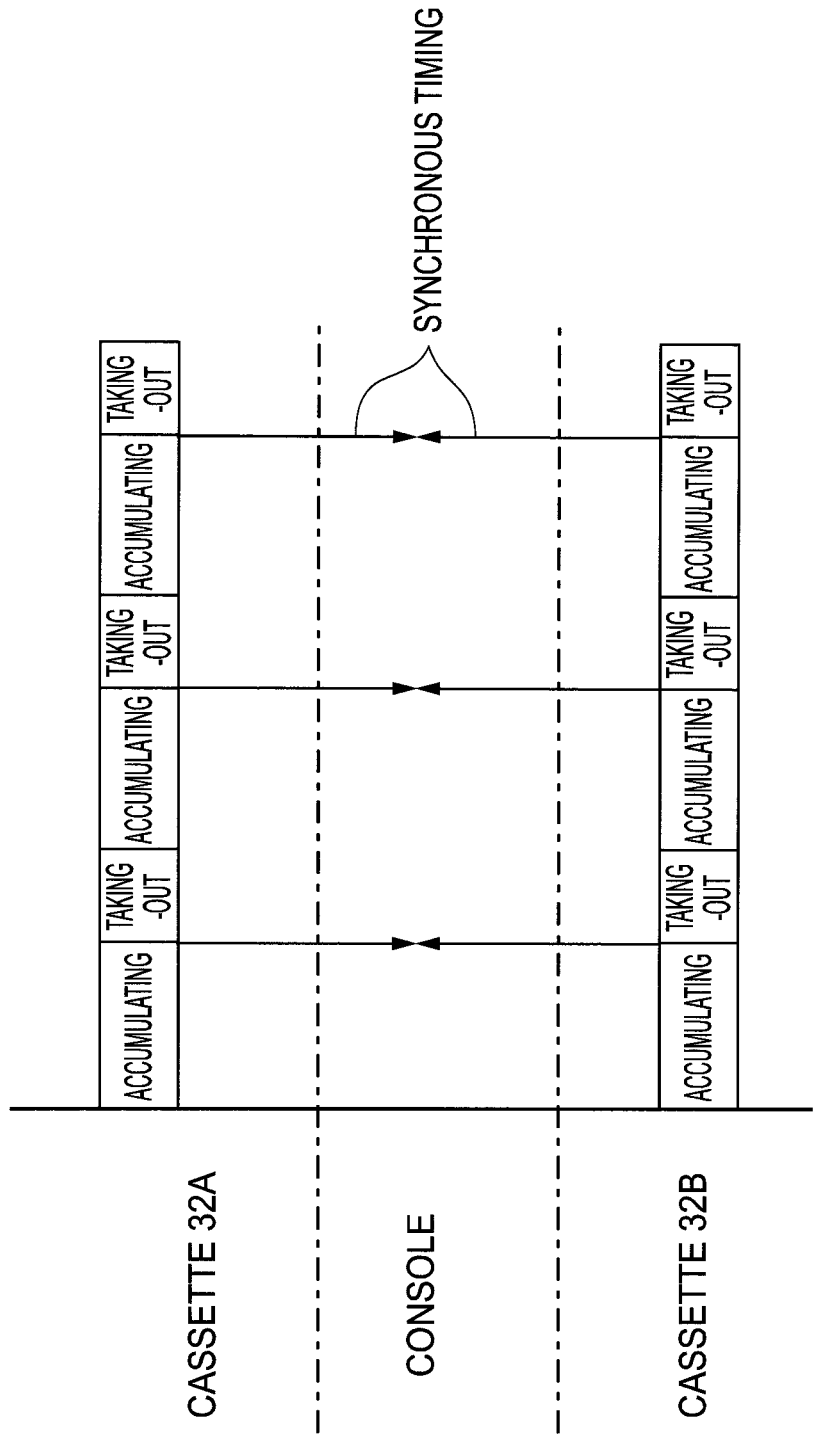
FIG. 18 is a plan view showing notification times of cycle timings of respective electronic cassettes relating to a third exemplary embodiment.

When the cassette controllers 92 of the respective electronic cassettes 32 relating to the present exemplary embodiment are repeatedly carrying out the accumulating/taking-out operations, as shown in FIG. 18, at each predetermined timing of the accumulating/taking-out operation of one frame (in the present exemplary embodiment, at the start of the taking-out operation), the cassette controller 92 notifies the console 42 of a cycle timing that expresses the cycle of the accumulating/taking-out operation. Note that the aforementioned predetermined timing may be the time of the end of the taking-out operation, or the time when a predetermined time period of the accumulating time period elapses.

In a case in which capturing of an elongated image is carried out, as shown in FIG. 9, the console 42 transmits the instruction information C1, the image capturing control information C3, and the request information C7 to the respective electronic cassettes 32, and carries out image capturing.

Further, in a case in which capturing of an elongated image is carried out, the console 42 judges, on the basis of the cycle timings notified from the respective electronic cassettes 32, whether or not the accumulating/taking-out operations of the respective electronic cassettes 32 are synchronous. If the image capturing instructing operation of the first step has been carried out with respect to the operation panel 102, the image capturing instructing operation of the second step becomes possible if the information C6 expressing completion of standby is received from the radiation generator 34 and the accumulating/taking-out operations of the respective electronic cassettes 32 are synchronous.

Figure 19:
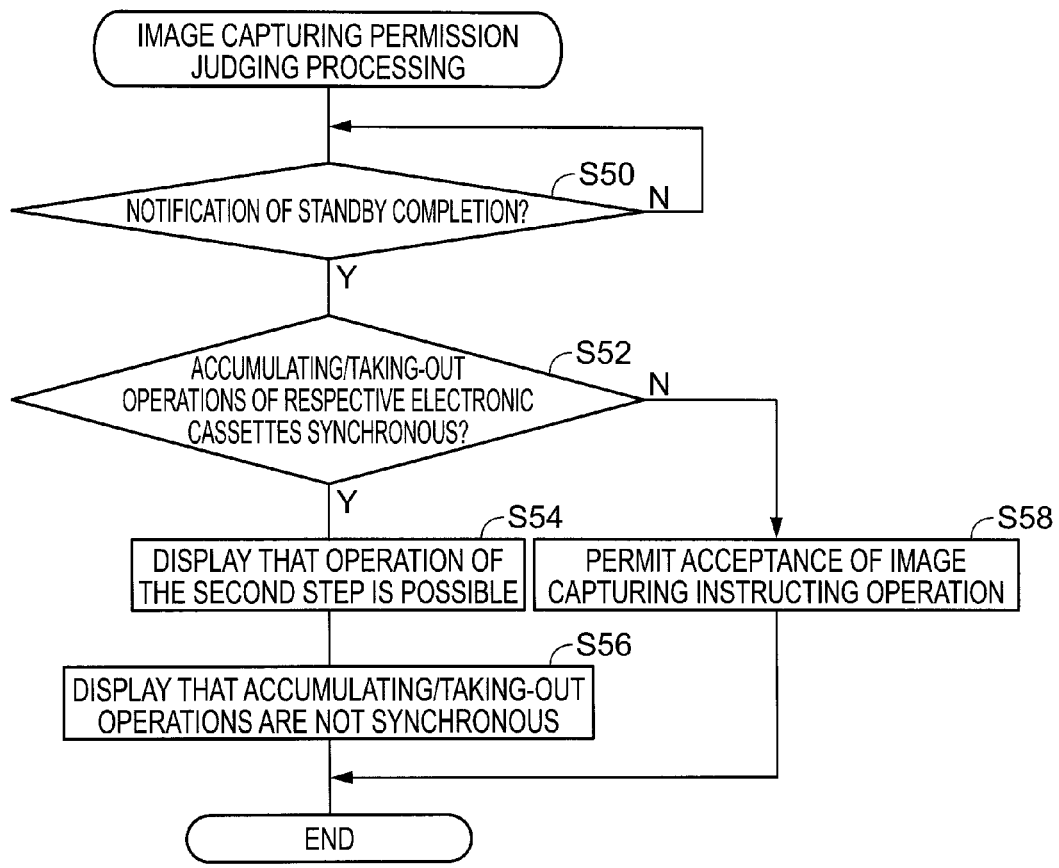
FIG. 19 is a flowchart showing the flow of an image capturing permission judging processing program relating to the third exemplary embodiment.

FIG. 19 shows the flow of image capturing permission judging processing that is executed by the CPU 104 at the time when the image capturing instructing operation of the first step has been carried out with respect to the operation panel 102.

In step S50, a judgment is made as to whether or not the information C6 expressing completion of standby has been received from the radiation generator 34. If the judgment is affirmative, the routine moves on to step S52. If the judgment is negative, the routine moves on again to step S50, and receipt of the information C6 is awaited.

In step S52, on the basis of the cycle timings that are notified from the respective electronic cassettes 32, a judgment is mare as to whether or not the accumulating/taking-out operations of the respective electronic cassettes 32 are synchronous. If the judgment is affirmative, the routine moves on to step S54. If the judgment is negative, the routine moves on to step S56.

Note that the judgment as to whether or not the operations are synchronous is carried out in accordance with whether or not the cycle timings notified from the respective electronic cassettes 32 are within a predetermined time difference. For this predetermined time difference, a range, that is obtained in advance by computer simulation or the like on the basis of experimentation in accordance with actual devices or specifications of actual devices, is used as the range in which it can be judged that the accumulating/taking-out operations of the respective electronic cassettes 32 are synchronous.

In step S54, the fact that the operation of the second step is possible is displayed on the display 100.

In next step S56, acceptance, at the operation panel 102, of the image capturing instructing operation that instructs image capturing is permitted, and the image capturing permission judging processing ends.

On the other hand, in step S58, the fact that the accumulating/taking-out operations of the respective electronic cassettes 32 are not synchronous is displayed on the display 100, and the image capturing permission judging processing ends.

As described above, in accordance with the present exemplary embodiment, in a case in which image capturing of radiographic images is to be carried out simultaneously at plural electronic cassettes 32, image capturing is not permitted if the accumulating/taking-out operations of the respective electronic cassettes 32 are not synchronous. Therefore, failed image capturing can be prevented.

Fourth Exemplary Embodiment

Next, a fourth exemplary embodiment will be described.

Since the configuration of a radiographic information system 10 and the internal configuration of electronic cassettes 32 according to the fourth exemplary embodiment is the same as those of the first exemplary embodiment (see FIGS. 1 to 8), explanations thereof are omitted.

Figure 28:
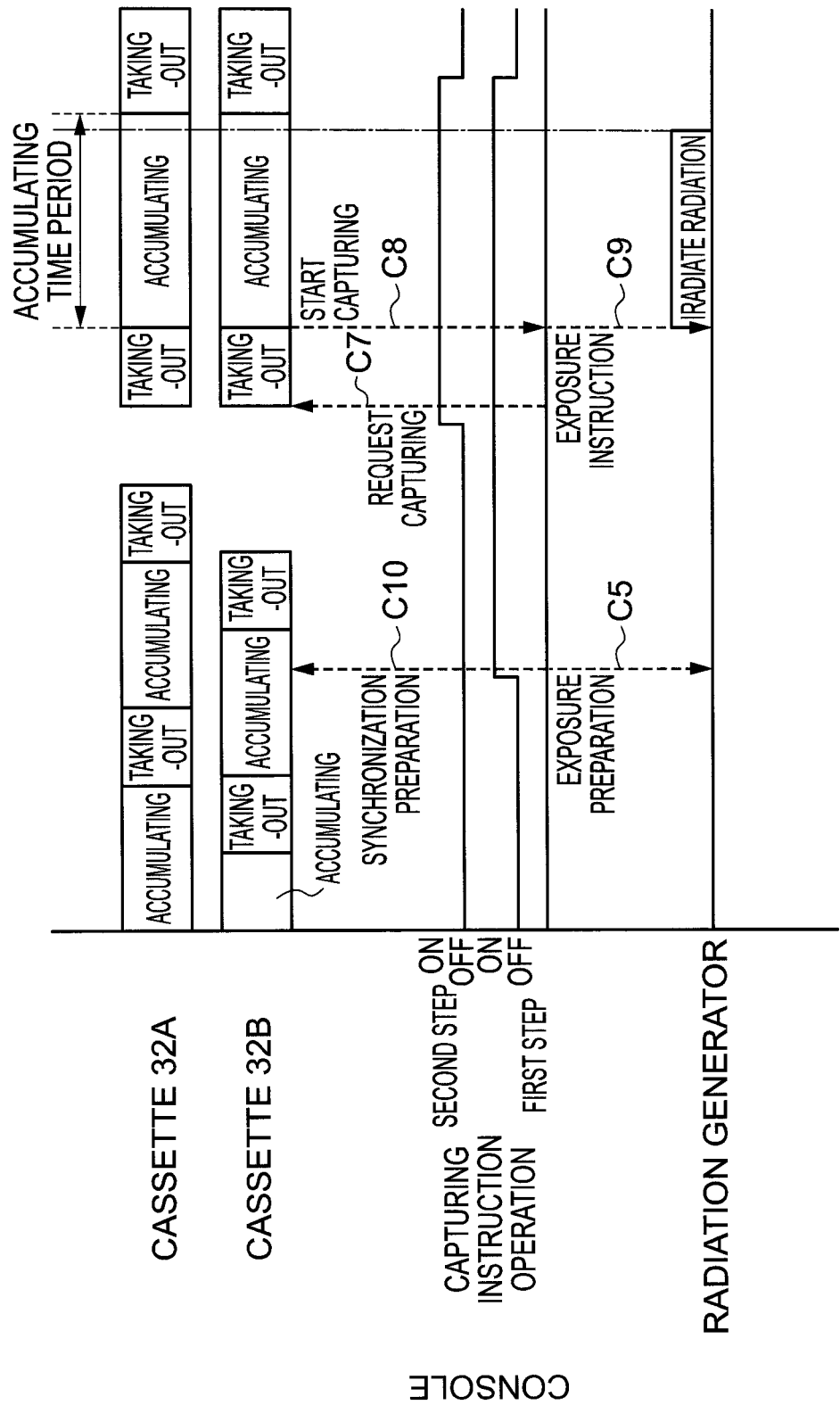
FIG. 28 is a timing chart showing an operation flow when a radiographic image is captured by a radiographic image capturing system according to a fourth exemplary embodiment.

FIG. 28 shows a timing chart indicating an operation flow when a radiographic image is captured by a capturing system 18 according to the fourth exemplary embodiment.

In two electronic cassettes 32A and 32B, in response to reception of instruction information C1 that instructs operation in the resetting mode, the operation mode shifts to the resetting mode, and the electronic cassettes 32A and 32B respectively carry out the accumulating/taking-out operation repeatedly. Therefore, the accumulating/taking-out operations in the electronic cassettes 32A and 32B may not be synchronized.

In the capturing system 18 of present exemplary embodiment, at the time when the image capturing instructing operation of the first step is carried out with respect to the operation panel 102, the console 40 transmits instruction information C10 that instructs synchronization preparations to the electronic cassettes 32A and 32B. Note that the timing of transmission of the instruction information C10 to the electronic cassettes 32A and 32B is not limited to the time when the image capturing instructing operation of the first step is carried out, and may be any time before capturing. The timing may be, for example, when capturing of an elongated image is specified to the two electronic cassettes 32A and 32B, but it is preferably at the time close to the time of capturing.

In response to the reception of the instruction information C10, the electronic cassettes 32A and 32B complete the accumulating/taking-out operation currently in progress, and wait without further performing the accumulating/taking-out operation.

In response to the reception of the request information C7 that requests permission to irradiate radiation for image capturing, the electronic cassettes 32A and 32B carry out the taking-out operation by sequentially outputting ON signals to each of the gate lines 76 one by one, taking out the charges accumulated in each of the pixels 74 of the radiation detector 60, and resetting one frame. After completion of the taking-out operation, the electronic cassettes 32A and 32B transmit, to the console 42, instruction information C8 that instructs starting of capturing, and shifts the operation mode to the image capturing mode.

That is, in the capturing system 18 of the fourth exemplary embodiment, operations of the electronic cassettes 32A and 32B are synchronized at the time of capturing.

According to the present embodiment, the electronic cassettes 32A and 32B can simultaneously perform capturing of a radiographic image without performing in advance the synchronous control processing that synchronizes the accumulating/taking-out operations of the electronic cassettes 32A and 32B.

Fifth Exemplary Embodiment

Next, a fifth exemplary embodiment will be described.

Since the configuration of a radiographic information system 10 and the internal configuration of electronic cassettes 32 according to the fifth exemplary embodiment is the same as those of the second exemplary embodiment (see FIGS. 1 to 4, 6, 7, 13 and 14), explanations thereof are omitted.

Also in the capturing system 18 of this exemplary embodiment, in a case in which capturing of an elongated image is carried out, as shown in FIG. 15, the electronic cassettes 32A to 32C are overlapped such that the optical communication portions 200 provided at the irradiated surface 56 of one electronic cassette 32 faces the optical communication portions 202 provided at the reverse 57 of the other electronic cassette 32.

In the capturing system 18 of the fifth exemplary embodiment, operations of the electronic cassettes 32A to 32C are synchronized at the time of capturing similarly as in the fourth exemplary embodiment. For example, the instruction information C10 that instructs synchronization preparations is transmitted to the electronic cassettes 32A to 32C at the time when the first step of capturing instruction operation is performed via the operation panel 102.

In response to the reception of the instruction information C10, the respective electronic cassettes 32 of the present exemplary embodiment detect the order of the overlapping based on the connection state of the communication portions 200 and 202, and perform the synchronous control processing that synchronizes the accumulating/taking-out operations of each of the electronic cassettes 32 based on the detection result. Note that the timing of performing the synchronous control processing is not limited to the time when the instruction information C10 is received, and may be any time before capturing, but preferably close to the time of capturing.

Figure 29:
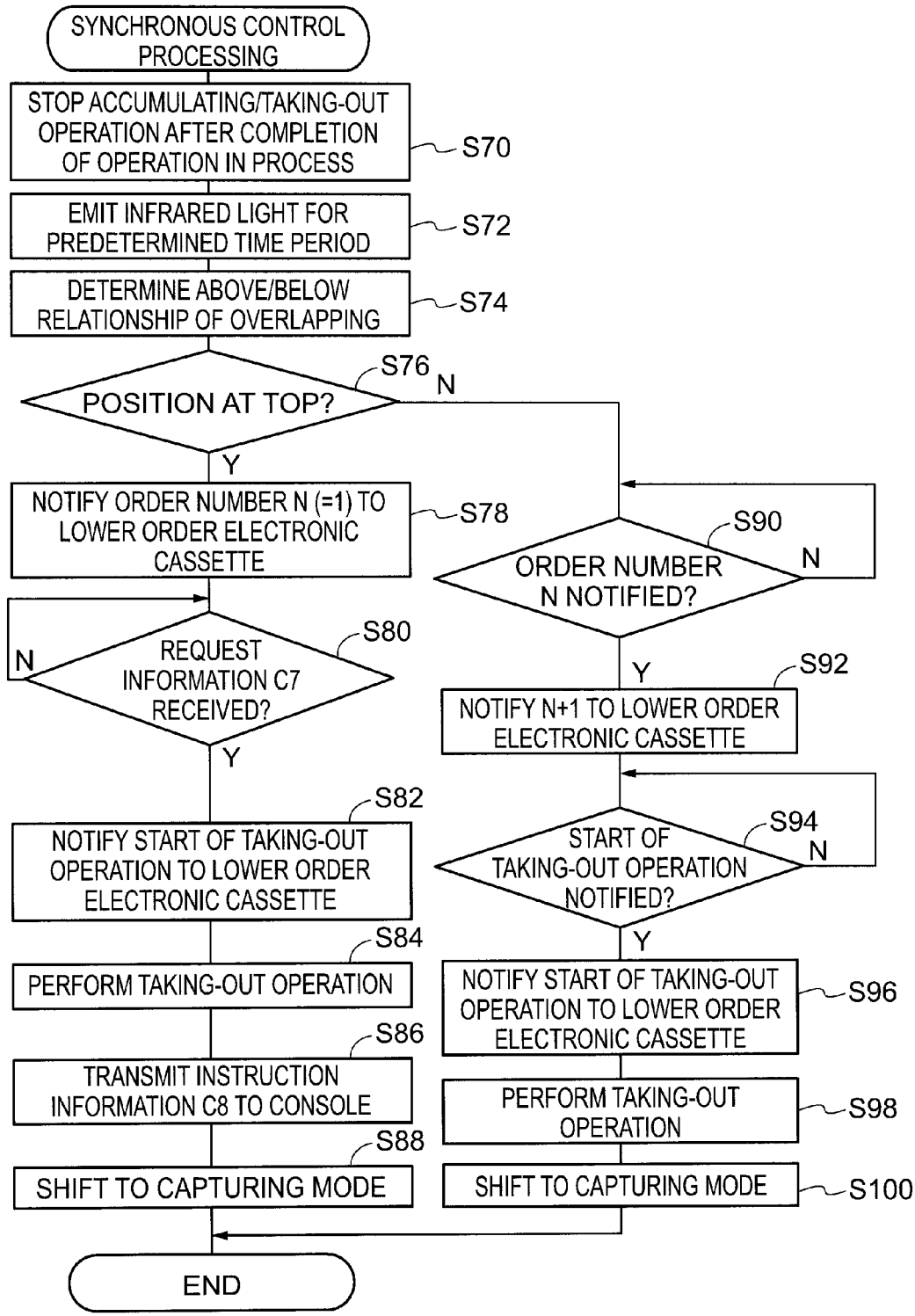
FIG. 29 is a flow chart showing a flow of a synchronous control processing program according to a fifth exemplary embodiment.

FIG. 29 shows a flow of the synchronous control processing which is performed by the CPU 92A of the cassette controller 92 of the respective electronic cassette 32 when the instruction information C10 has been received.

In step S70, the electronic cassette 32 completes the accumulating/taking-out operation currently in progress, and waits without further performing the accumulating/taking-out operation.

In step S72, infrared light is emitted for a predetermined time period from the light-emitting portion 200A of the optical communication portion 200 and the light-emitting portion 200A of the optical communication portion 202.

In the next step S74, based on the detection result at the light-receiving portion 200B of the optical communication portion 200 and the light-receiving portion 200B of the optical communication portion 202, above/below relationships of the overlapping of the electronic cassettes 32 are determined. That is, if infrared light is not detected at the light-receiving portion 200B, there is no electronic cassette 32 overlapping on the irradiated surface 56, and if infrared light is detected at the light-receiving portion 200B, there is an electronic cassette 32 overlapping on the irradiated surface 56. Similarly, if infrared light is not detected at the light-receiving portion 202B, there is no electronic cassette 32 overlapping on the reverse 57, and if infrared light is detected at the light-receiving portion 202B, there is an electronic cassette 32 overlapping on the reverse 57.

In this manner, a determination can be made such that, for example, if the electronic cassettes 32A to 32C are overlapped as shown in FIG. 15, the electronic cassette 32A is positioned at the top.

In the next step 76, a determination is made as to whether the electronic cassette 32 performing this processing is positioned at the top in the above/below relationships determined at step 74. If the determination is affirmative, the processing proceeds to step 78, and if the determination is negative, the processing proceeds to step 90.

In step 78, since the electronic cassette 32 carrying out the processing is positioned at the top, order number N of the overlapping is determined to be 1, and the order number N is notified to an electronic cassette 32 below by emitting light from the light-emitting portion 202A of the optical communication portion 200 in order to determine the order number N of the electronic cassette 32 below.

In step 80, a determination is made as to whether the request information C7 that requests permission to irradiate radiation for image capturing has been received. If the determination is affirmative, the processing proceeds to step 82, and if the determination is negative, the processing returns to step 80 and reception of the request information C7 is awaited.

In step 82, the electronic cassette 32 notifies the electronic cassette 32 of lower order (i.e., having a larger order number N) of the start of the taking-out operation by emitting light from the light-emitting portion 202A.

In the next step 84, the electronic cassette 32 performs the taking-out operation by outputting ON signals to each of the gate lines 76 line by line, taking out the charges accumulated in each of the pixels 74 of the radiation detector 60, and resetting one frame.

In the next step 86, after completion of the taking-out operation in step 84, the electronic cassette 32 transmits to the console 42 the instruction information C8 that instructs the start of capturing.

In step 88, the electronic cassette 32 shifts the operation mode to capturing mode and starts capturing, and terminates the present synchronous control processing.

In step 90, the electronic cassette 32 waits for a notification of the order number N to the light-receiving portion 200B of the optical communication portion 200 from the upper order electronic cassette 32 which is overlapped thereon.

In step 92, the electronic cassette 32 determines its own order number N by adding 1 to the notified order number N (i.e., N+1), and notifies an electronic cassette 32 of lower order of its own determined own order number N by emitting light from the light-emitting portion 202A.

Thus, when the three electronic cassettes 32A to 32C are overlapped as shown in FIG. 15, for example, the electronic cassettes 32A is determined as N=1, the electronic cassettes 32B is determined as N=2, and the electronic cassettes 32C is determined as N=3.

In step 94, a determination is made as to whether the start of the taking-out operation has been notified from the upper order electronic cassette 32. If the determination is affirmative, the processing proceeds to step 96, and if the determination is negative, the processing returns to step 94.

In step 96, the electronic cassette 32 notifies the lower order electronic cassette 32 the start of the taking-out operation by emitting light from the light-emitting portion 202A.

In step 98, the electronic cassette 32 performs the taking-out operation by outputting ON signals to each of the gate lines 76 line by line, taking out charges accumulated in each of the pixels 74 of the radiation detector 60, and resetting one frame.

In the next step 100, after completion of the taking-out operation in step 98, the electronic cassette 32 shifts the operation mode to the capturing mode, and terminates the present synchronous control processing.

In this manner, as shown in FIG. 30, three electronic cassettes 32A to 32C can perform capturing in synchronization.

That is, in the capturing system 18 of the fifth exemplary embodiment, when capturing, the electronic cassette 32A serves as a master device, the electronic cassettes 32B and 32C serve as slave devices, and the electronic cassette 32A which is the master device conducts synchronization of operations of the electronic cassettes 32B and 32C which are the slave devices. Further, the electronic cassette 32A as the master device transmits to the console 42 the instruction information C8 that instructs a start of capturing as a representative of the electronic cassettes 32A to 32C.

According to the present embodiment, the electronic cassettes 32A to 32C can simultaneously perform capturing of a radiographic image without performing in advance the synchronous control processing that synchronizes the accumulating/taking-out operations of the electronic cassettes 32A to 32C.

Note that the third exemplary embodiment describes a case in which the respective electronic cassettes 32 notify the console 42 of the cycle timings, and, on the basis of the cycle timings notified from the respective electronic cassettes 32, the console 42 judges whether or not the accumulating/taking-out operations of the respective electronic cassettes 32 are synchronous. However, the present invention is not limited to the same. For example, in a case in which the plural electronic cassettes 32 are superposed as in the second exemplary embodiment, the electronic cassettes 32 whose order numbers N are N=2 and greater may give notice of the cycle timing of its own accumulating/taking-out operation to the electronic cassette 32 whose order number N is smaller than its own, and also notify the electronic cassette 32 whose order number N is smaller than its own of the cycle timings that are notified from the electronic cassettes 32 whose order numbers N are greater than its own. Due thereto, for example, in a case in which the three electronic cassettes 32A through 32C are overlapped as shown in FIG. 15, the cycle timing of the electronic cassette 32B is notified to the electronic cassette 32A, and the cycle timing of the electronic cassette 32C is notified to the electronic cassette 32A via the electronic cassette 32B. The console 42 may ask the electronic cassette 32 whose order number is N=1 whether the accumulating/taking-out operations of the respective electronic cassettes 32 are synchronous. On the basis of the cycle timings informed from the respective electronic cassettes 32, the electronic cassette 32 whose order number is N=1 may judge whether or not the accumulating/taking-out timings of the respective electronic cassettes 32 are synchronous, and send the results of judgment to the console 42 as a reply. Further, also in the second exemplary embodiment, the respective electronic cassettes 32 may notify the console 42 of the cycle timings, and the console 42 may judge whether or not the accumulating/taking-out operations of the respective electronic cassettes 32 are synchronous.

The third exemplary embodiment describes a case in which, when the image capturing instructing operation of the first step has been carried out with respect to the operation panel 102, a judgment is made as to whether or not the accumulating/taking-out operations of the respective electronic cassettes 32 are synchronous. However, the present invention is not limited to the same. For example, on the basis of the cycle timings notified from the respective electronic cassettes 32, the console 42 may at any time judge whether or not the accumulating/taking-out operations of the respective electronic cassettes 32 are synchronous, and may at any time display the results of judgment on the display 100. Further, notification of the results of judgment may be given by a sound, a lamp, or the like.

The respective exemplary embodiments describe cases in which the accumulating/taking-out operation, that takes-out the charges accumulated in the respective pixels 74 of the radiation detector 60 after an accumulating time period has elapsed, is carried out as the image capturing preparation operation that is carried out periodically. However, the present invention is not limited to the same. The accumulating/taking-out operation may be an operation that repeatedly takes-out the charges accumulated in the respective pixels 74 of the radiation detector 60, without waiting for an accumulating time period to elapse.

The first exemplary embodiment describes a case in which synchronizing of the electronic cassettes 32A, 32B is carried out by, via the console 42, notifying the electronic cassette 32B of the operation timing of the accumulating/taking-out operation of the electronic cassette 32A. However, the present invention is not limited to the same. For example, the console 42 may notify the electronic cassettes 32A, 32B of the respective operation timings of the accumulating/taking-out operations, and the electronic cassettes 32A, 32B may operate in accordance with the notified operation timings.

In the above second exemplary embodiment as well, the console 42 may notify the electronic cassettes 32A through 32C of the respective operation timings of the accumulating/taking-out operations, and the electronic cassettes 32A through 32C may operate in accordance with the notified operation timings.

Further, although the first exemplary embodiment describes a case in which the communication between the console 42 and the electronic cassettes 32 is wired communication, and the second exemplary embodiment describes a case in which the communication between the console 42 and the electronic cassettes 32 is radio communication, the present invention is not limited to the same. For example, the communication between the console 42 and the electronic cassettes 32 in the first exemplary embodiment may be radio communication, and the communication between the console 42 and the electronic cassettes 32 in the second exemplary embodiment may be wired communication. If the communication between the console 42 and the electronic cassettes 32 is wired communication in the second exemplary embodiment, for example, a communication cable may be connected to one of the electronic cassettes 32 only so as to communicate by wire with this electronic cassette 32, and the other electronic cassettes 32 may carry out optical communication with the electronic cassette 32 connected to the communication cable, and may communicate with the console 42 via this electronic cassette 32 connected to the communication cable.

Although the second exemplary embodiment describes a case in which notification of the operation timings among the electronic cassettes 32 is carried out by optical communication, the present invention is not limited to the same. For example, contact-type communication terminals or magnetic couplers may be provided at the respective electronic cassettes 32, and communication may be carried out electrically or magnetically. By making the communication between the electronic cassettes 32 be one-to-one communication in this way, the ability to operate in real time is improved. Further, by making the communication between the electronic cassettes 32 be short range communication such as infrared ray communication or magnetic couplers or the like, there are also the effects that interference is prevented and disturbance is prevented.

Figure 20:
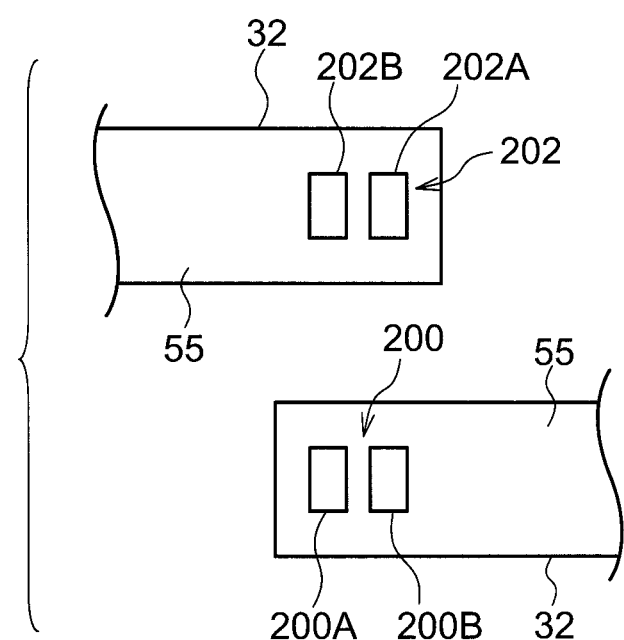
FIG. 20 is a plan view showing the placement of optical communication portions of electronic cassettes relating to another exemplary embodiment.
Figure 21:
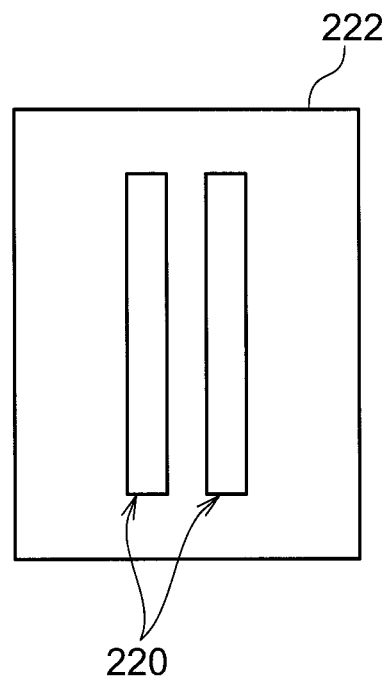
FIG. 21 is a plan view showing the structure of a connecting member that connects optical communication portions of electronic cassettes relating to another exemplary embodiment.
Figure 22:
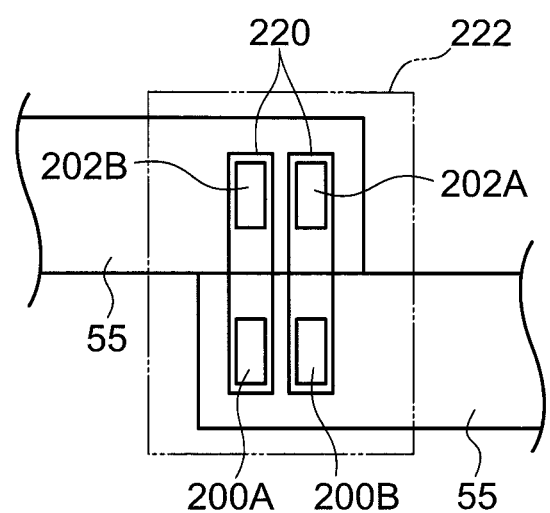
FIG. 22 is a plan view showing the placed state at the time of carrying out optical communication between electronic cassettes relating to another exemplary embodiment.

Further, the second exemplary embodiment describes a case in which the optical communication portion 200 is provided at the irradiated surface 56 of the casing 54 of the electronic cassette 32, and the optical communication portion 202 is provided at the reverse 57 of the casing 54. However, the present invention is not limited to the same. For example, as shown in FIG. 20, the optical communication portion 200 and the optical communication portion 202 may be provided at a side surface 55 of the casing 54. In this case, as shown in FIG. 21 and FIG. 22, the electronic cassettes 32 may be fixed by a connecting member 222 at which are provided two light guiding members 220 that guide infrared light, so that the light of the light-emitting portion 200A of the optical communication portion 200 is received at the light-receiving portion 202B of the optical communication portion 202, and the light of the light-emitting portion 202A of the optical communication portion 202 is received at the light-receiving portion 200B of the optical communication portion 200.

Figure 23:
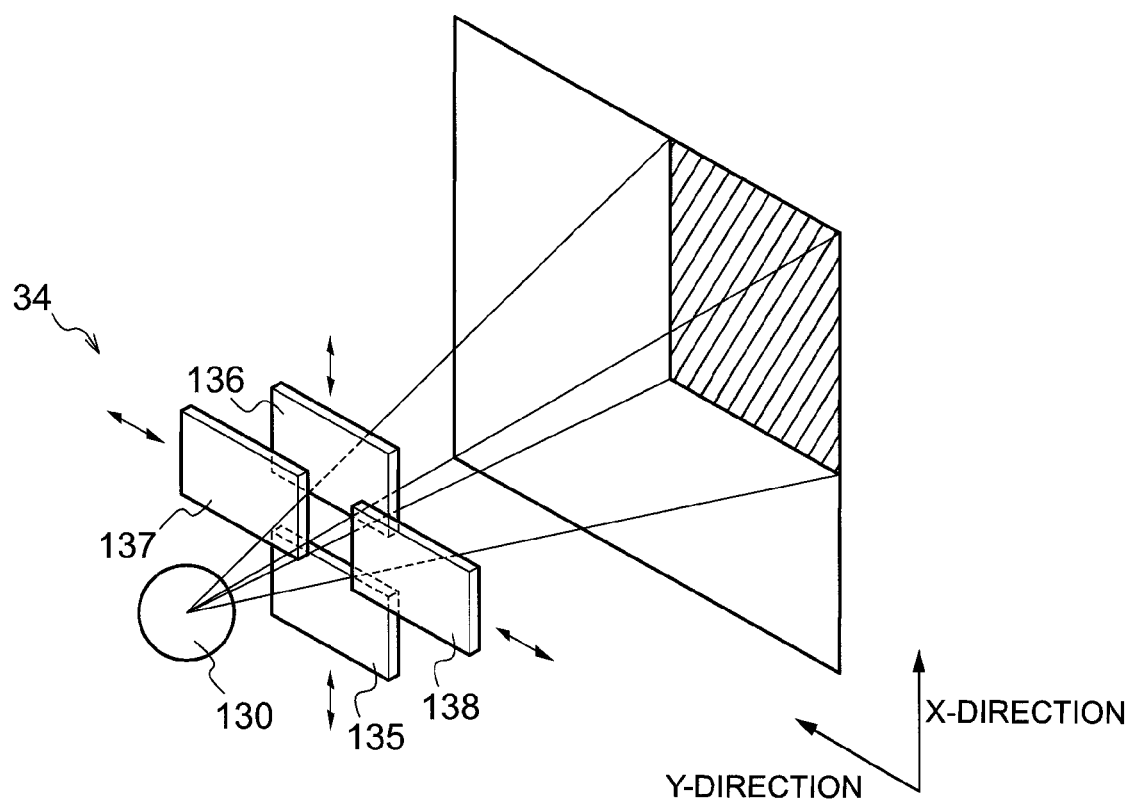
FIG. 23 is a perspective view showing the schematic structure of a radiation generator relating to another exemplary embodiment.

Further, although the above respective exemplary embodiments describe cases in which the accumulating/taking-out operations of the respective electronic cassettes 32 are synchronized, the present invention is not limited to the same. For example, as shown in FIG. 23, the region onto which the radiation X is irradiated may be changed in accordance with the image capturing region by providing, at the radiation generator 34, slit plates 135, 136 that change in the X-direction the irradiation region of the radiation X by the radiation source 130 by moving relatively in one direction (the X-direction) with respect to the irradiated surface 56 of the electronic cassette 32, and slit plates 137, 138 that change in the Y-direction the irradiation region of the radiation X by the radiation source 130 by moving relatively in an intersecting direction (the Y-direction) with respect to the irradiated surface 56 of the electronic cassette 32.

For example, in the first exemplary embodiment, in a case in which one electronic cassette 32 is accommodated in the accommodating portion 46A of the image capturing stand 45 and image capturing is carried out, the region may be limited such that the radiation X is irradiated from the irradiation source 130 onto a portion of the image capturing stand 45. In a case in which two electronic cassettes 32 are used and one electronic cassette 32 is accommodated in the accommodating portion 46A of the image capturing stand 45 and the other electronic cassette 32 is engaged with the hooks 46B of the image capturing stand 45 and image capturing of an elongated image is carried out, the region may be limited such that the radiation X is irradiated also onto the electronic cassette 32 that is engaged with the hooks 46B. It suffices for the console 42 to control the radiation generator 34 such that, in a case in which one of the electronic cassettes 32 is connected, the electronic cassette 32 is accommodated in the accommodating portion 46A of the image capturing stand 45 and image capturing is carried out, and, in a case in which two of the electronic cassettes 32 are connected, capturing of an elongated image is carried out.

Further, for example, in the second exemplary embodiment, the region may be limited such that the radiation X is irradiated onto the image capturing regions of the respective electronic cassettes 32 in accordance with the amounts (areas) of overlap of the respective electronic cassettes 32.

Figure 24:
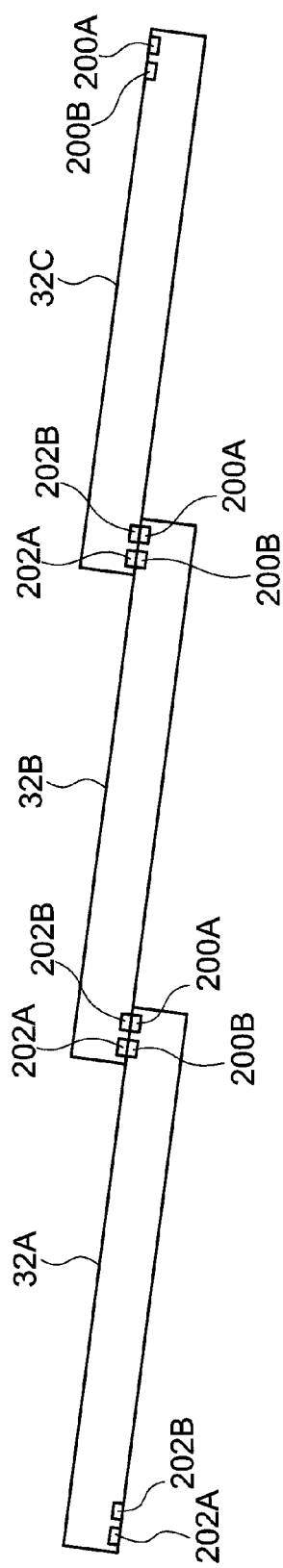
FIG. 24 is a drawing showing an example in which plural electronic cassettes relating to another exemplary embodiment are overlapped.
Figure 25:
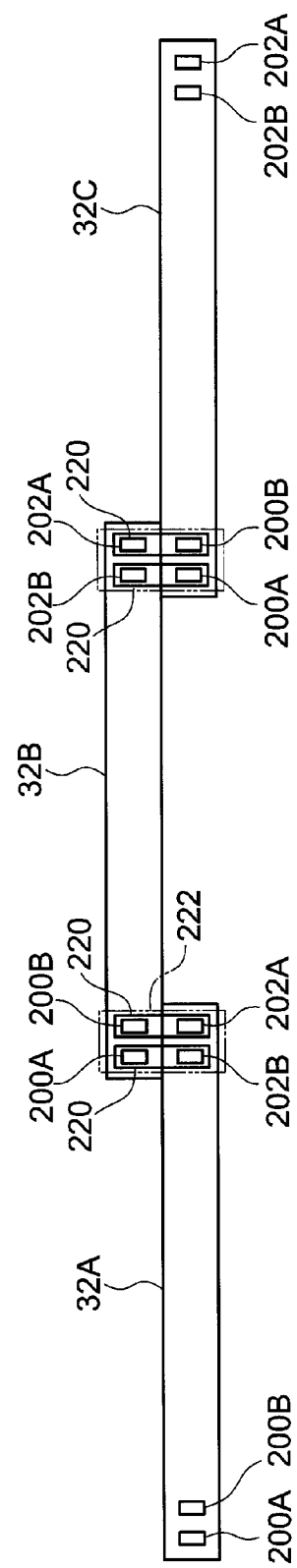
FIG. 25 is a drawing showing an example in which plural electronic cassettes relating to another exemplary embodiment are overlapped.
Figure 26:
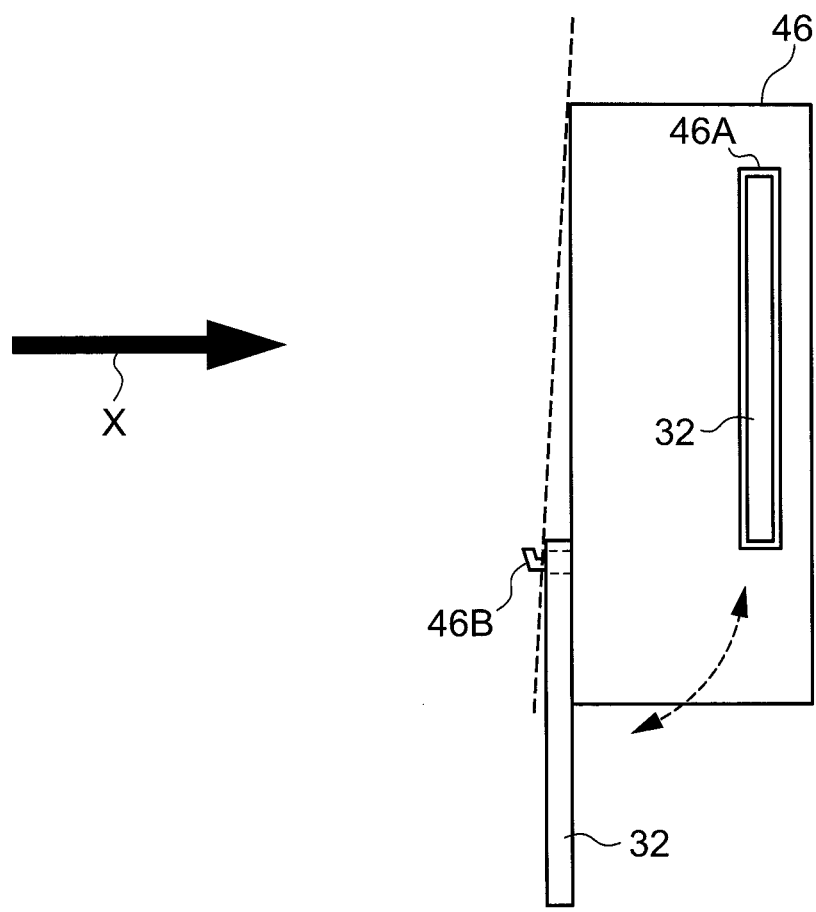
FIG. 26 is a drawing showing a structure in a case in which an image capturing section relating to another exemplary embodiment is tilted.

Although the second exemplary embodiment describes a case in which the electronic cassettes 32 are overlapped in order and in parallel, the present invention is not limited to the same. For example, as shown in FIG. 24, the respective electronic cassettes 32 may be tilted and overlapped. In a case in which the electronic cassettes 32 are overlapped in parallel, the greater the number of the electronic cassettes 32, the more the overall thickness increases, and, the further away from the patient 30, the more the captured image is enlarged. However, by tilting and overlapping the electronic cassettes 32, the overall thickness can be suppressed, and the difference in the enlargement rates of the three images that are captured can be suppressed. Further, in a case in which the optical communication portion 200 and the optical communication portion 202 are provided at the side surface 55 of the casing 54 as shown in FIG. 20, the respective electronic cassettes 32 may be disposed alternately and fixed by the connecting members 222, as shown in FIG. 25. In this case as well, the overall thickness can be suppressed. Further, in the first exemplary embodiment as well, at the image capturing stand 45, as shown in FIG. 26, the image capturing section 46 may be tilted such that the dashed line becomes vertical, and the overall thickness is suppressed and the difference in the enlargement rates of the two captured images is suppressed.

Further, in the fourth and fifth exemplary embodiments, it has been described that in response to the reception of the request information C7 that requests permission to irradiate radiation for image capturing, the electronic cassette 32 performs the taking-out operation that resets one frame and then shifts to the capturing mode. However, embodiments are not limited thereto. For example, the electronic cassette 32 may shift to the capturing mode after performing the accumulating/taking-out operation, or may perform further processing before shifting to the capturing mode. In a case in which the accumulating/taking-out operation is performed, information on dark-current noise at a time just before capturing can be obtained.

Figure 27:
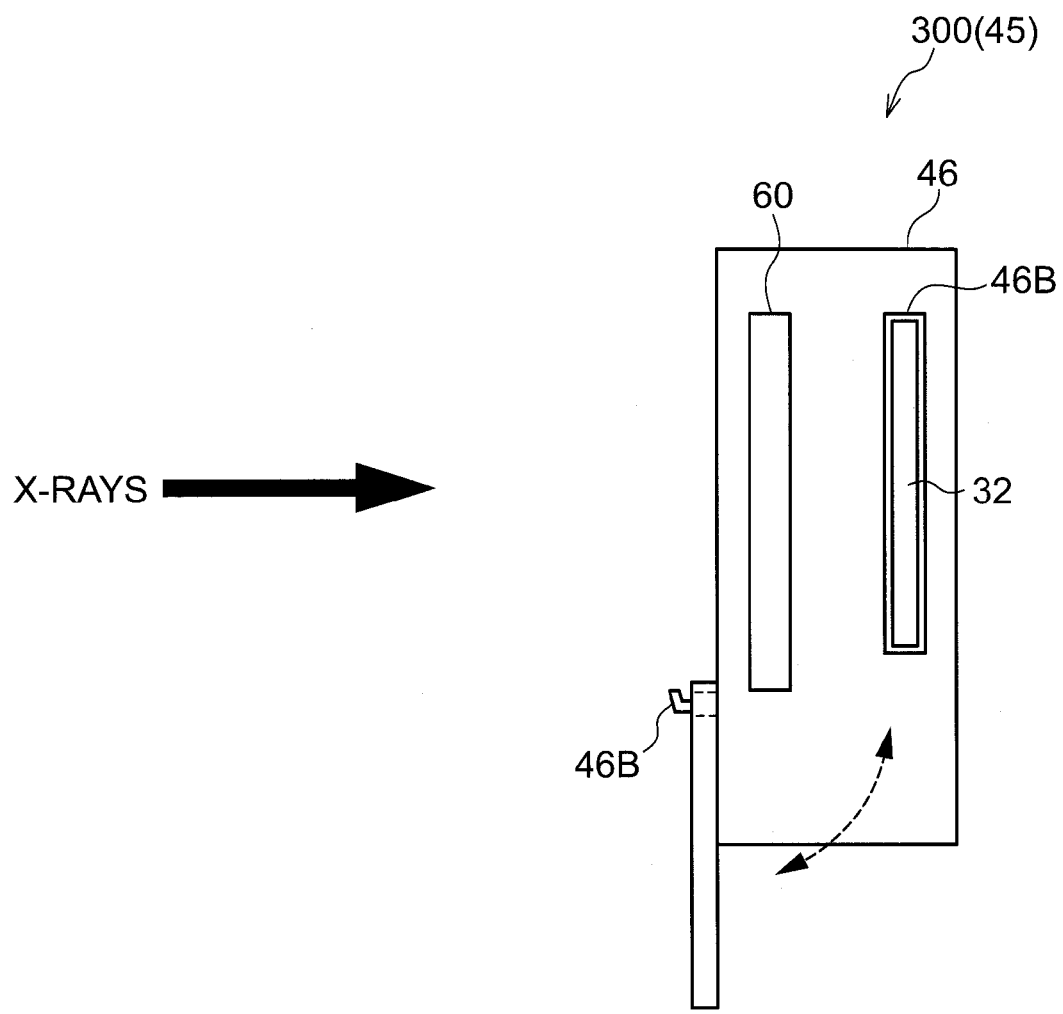
FIG. 27 is a drawing showing the schematic structure of a stationary radiographic image capturing device relating to another exemplary embodiment.

Although the above exemplary embodiments describe cases that are applied to the electronic cassettes 32 that are portable radiographic image capturing devices, the present invention is not limited to the same. The present invention may be applied at the time of capturing an elongated image by combining the electronic cassette 32 and a stationary radiographic image capturing device. For example, as shown in FIG. 27, the image capturing stand 45 may be structured as a stationary radiographic image capturing device 300 in which the radiation detector 60 is incorporated within the image capturing section 46 and at which a radiographic image can be captured by control from the console 42. In this radiographic image capturing device 300, in a case in which an image of the chest region or the like is captured in a standing state, image capturing may be carried out by the radiation detector 60 incorporated in the image capturing section 46, and, in a case in which an elongated image such as the hip region, the leg region, or the like from the chest region is captured, the electronic cassette 32 may be engaged with the hooks 46B of the image capturing section 46, and elongated image capturing may be carried out by the electronic cassette 32 and the radiation detector 60 that is incorporated within the image capturing section 46. At this time, the electronic cassette 32 may be connected to the stationary radiographic image capturing device 300, and may carry out communication with the console 42 via the radiographic image capturing device 300. The electronic cassette 32 may receive a power supply from the stationary radiographic image capturing device. The accommodating portion 46A provided at the image capturing section 46 may function as a cradle that charges a battery that is incorporated within the accommodated electronic cassette 32. The electronic cassette 32 may transmit the image information expressing the captured radiographic image to the console 42 when the electronic cassette 32 is accommodated in the accommodating portion 46A and the connection terminal 32A can communicate with the connection terminal 46C.

Moreover, the structure of the RIS 10 (see FIG. 1), the structure of the image capturing stand 45 (see FIG. 2, FIG. 4, FIG. 6, and FIG. 27), the structure of the electronic cassette 32 (see FIG. 5, FIG. 13, FIG. 15, FIG. 16, and FIG. 20 through FIG. 22), the structure of the image capturing system 18 (see FIG. 7, FIG. 18 and FIG. 14), and the structure of the radiation generator 34 (see FIG. 23) that are described in the above respective exemplary embodiments are examples. Unnecessary portions may be eliminated therefrom, new portions may be added thereto, or the states of connection may be changed, within a scope that does not deviate from the gist of the present invention.

The flow of the operation at the time of radiographic image capturing that is described in the above exemplary embodiments (see FIGS. 9, 10, 18, 28, 30) also is an example, and can be changed in accordance with the situation within a scope that does not deviate from the gist of the present invention.

Further, the flows of the processings of the synchronous control processing programs (see FIGS. 11, 17, and 29) and the flow of the processing of the image capturing permission judging processing program (see FIG. 19) also are examples, and unnecessary steps may be eliminated therefrom, new steps may be added thereto, or the order of the processings may be rearranged, within a scope that does not deviate from the gist of the present invention.

What is claimed is:

1. A radiographic image capturing system comprising:
    a plurality of radiographic image capturing devices that carry out image capturing preparation operations when capturing a radiographic image, wherein the radiographic image capturing devices are disposed along different optical axes of radiation with respect to at least one of a radiation source or an image capturing position;
    a synchronous control section that carries out control that synchronizes the image capturing preparation operations of the plurality of radiographic image capturing devices;
    a detecting section that detects degrees of overlap of radiographic image capturing regions of the plurality of radiographic image capturing devices; and
    a limiting section that limits a region onto which radiation is irradiated from the radiation source, in accordance with the degrees of overlap of the radiographic image capturing regions detected by the detecting section.

2. The radiographic image capturing system of claim 1, further comprising:
    a judging section that judges whether or not the image capturing preparation operations of the plurality of radiographic image capturing devices are synchronous; and
    a permitting section that permits irradiation of radiation onto the plurality of radiographic image capturing devices, in a case in which the judging section judges that the image capturing preparation operations are synchronous.

3. The radiographic image capturing system of claim 1, further comprising:
    a judging section that judges whether or not the image capturing preparation operations of the plurality of radiographic image capturing devices are synchronous; and
    a notification section that gives notice of results of judgment by the judging section.

4. The radiographic image capturing system of claim 1, wherein the plurality of radiographic image capturing devices are positioned to provide data corresponding to a different portion of a single, elongated image of an object of radiation at the image capturing position.

5. The radiographic image capturing system of claim 1, wherein the synchronous control section synchronizes the image capturing preparation operations of the plurality of radiographic image capturing devices by notifying the plurality of radiographic image capturing devices of a cycle to be synchronized with, or by once suspending the image capturing preparation operations and re-starting the image capturing preparation operations in synchronization.

6. The radiographic image capturing system of claim 1, wherein each radiographic image capturing device comprises:
    a radiation detector having a plurality of sensor portions that accumulate charges generated due to radiation being irradiated from the radiation source; and
    a detector control section that controls the radiation detector to repeatedly carry out, as the image capturing preparation operation, an accumulating/taking-out operation that takes-out charges accumulated in the respective sensor portions of the radiation detector in a state in which radiation is not irradiated from the radiation source,
    wherein the synchronous control section synchronizes cycles of the accumulating/taking-out operations of the plurality of radiographic image capturing devices.

7. The radiographic image capturing system of claim 1, wherein the synchronous control section synchronizes the cycles of the accumulating/taking-out operations of other radiographic image capturing devices with the cycle of the accumulating/taking-out operation of any one of the radiographic image capturing devices.

8. The radiographic image capturing system of claim 1, wherein
    the synchronous control section is provided at each of the radiographic image capturing devices; and
    each radiographic image capturing device further comprises a communication unit that makes possible communication with the synchronous control sections provided at the respective radiographic image capturing devices.

9. A radiographic image capturing system comprising:
    a plurality of radiographic image capturing devices that carry out image capturing preparation operations;
    a synchronous control section that carries out control that synchronizes the image capturing preparation operations of the plurality of radiographic image capturing devices, in a case of capturing radiographic images simultaneously with the plurality of radiographic image capturing devices to obtain a single elongated image;
    a detecting section that detects degrees of overlap of radiographic image capturing regions of the plurality of radiographic image capturing devices; and
    a limiting section that limits a region onto which radiation is irradiated from the radiation source, in accordance with the degrees of overlap of the radiographic image capturing regions detected by the detecting section.

10. The radiographic image capturing system of claim 9, wherein each of the plurality of radiographic image capturing devices is positioned to provide data corresponding to a different portion of the single elongated image of an object of radiation at the image capturing position.

* * * * *